(12) United States Patent
Suzuki et al.

(10) Patent No.: US 12,208,222 B2
(45) Date of Patent: Jan. 28, 2025

(54) GUIDE WIRE HOLDER

(71) Applicant: OLYMPUS CORPORATION, Hachioji (JP)

(72) Inventors: Takahiro Suzuki, Tokyo (JP); Tomofumi Katayama, Tokyo (JP); Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1012 days.

(21) Appl. No.: 17/150,655

(22) Filed: Jan. 15, 2021

(65) Prior Publication Data

US 2021/0128889 A1     May 6, 2021

Related U.S. Application Data

(63) Continuation of application No. PCT/JP2019/001430, filed on Jan. 18, 2019.

(51) Int. Cl.
*A61M 25/09* (2006.01)
*A61F 2/966* (2013.01)
(Continued)

(52) U.S. Cl.
CPC ....... *A61M 25/09041* (2013.01); *A61F 2/966* (2013.01); *A61B 1/273* (2013.01);
(Continued)

(58) Field of Classification Search
CPC .. A61M 25/09041; A61M 2025/09116; A61M 2025/09125; A61M 2025/09183; A61M 2025/0177

See application file for complete search history.

(56) References Cited

U.S. PATENT DOCUMENTS

2004/0039250 A1   2/2004 Tholfsen et al.
2004/0044350 A1*  3/2004 Martin ............... A61B 18/1492
                                                   606/139
(Continued)

FOREIGN PATENT DOCUMENTS

EP   3238641 A1    11/2017
EP   3238642 A1 *  11/2017   ....... A61B 17/22031
(Continued)

OTHER PUBLICATIONS

Mar. 25, 2022 Search Report issued in European Patent Application No. 19838277.2.
(Continued)

*Primary Examiner* — Robert J Utama
*Assistant Examiner* — Neeraja Gollamudi
(74) *Attorney, Agent, or Firm* — Oliff PLC

(57) ABSTRACT

A guide wire holder includes a sheath having a lumen, an operation wire which is inserted through the lumen to be able to advance and retract, and a hook which is continuous with a distal end of the operation wire and protrudes from a distal end of the sheath, wherein the sheath has an inner wall surface which forms a groove configured to extend from the distal end of the sheath to a proximal end side of the sheath, the groove has an opening portion which opens to an outer peripheral surface of the sheath, the hook has a guide wire engagement surface which is engageable with a guide wire, and the guide wire is able to be held between the guide wire engagement surface and the inner wall surface.

13 Claims, 21 Drawing Sheets

(51) Int. Cl.
  *A61M 25/01* (2006.01)
  *A61B 1/273* (2006.01)
  *A61F 2/04* (2013.01)
  *A61M 5/00* (2006.01)

(52) U.S. Cl.
  CPC ........ *A61F 2002/041* (2013.01); *A61M 5/007* (2013.01); *A61M 2025/015* (2013.01); *A61M 2025/09116* (2013.01); *A61M 2025/09125* (2013.01); *A61M 2025/09183* (2013.01); *A61M 2210/1057* (2013.01)

(56) References Cited

U.S. PATENT DOCUMENTS

| | | | |
|---|---|---|---|
| 2013/0172855 A1 | 7/2013 | Wood et al. | |
| 2016/0121083 A1 | 5/2016 | Yokota et al. | |
| 2017/0246431 A1* | 8/2017 | Yokota | A61B 17/28 |
| 2018/0042462 A1 | 2/2018 | Yanuma | |

FOREIGN PATENT DOCUMENTS

| | | |
|---|---|---|
| JP | 2004-202006 A | 7/2004 |
| JP | 2015-506722 A | 3/2015 |
| JP | 2016-140630 A | 8/2016 |
| JP | 2017-169783 A | 9/2017 |
| WO | 2005/011788 A1 | 2/2005 |
| WO | 2013/071938 A1 | 5/2013 |
| WO | 2016/103897 A1 | 6/2016 |
| WO | 2016/103900 A1 | 6/2016 |

OTHER PUBLICATIONS

Apr. 9, 2019 International Search Report issued in International Patent Application No. PCT/JP2019/001430.

Oct. 23, 2018 International Search Report issued in International Patent Application No. PCT/JP2018/027283.

Aug. 17, 2021 Office Action issued in Japanese Patent Application No. 2020-530882.

* cited by examiner

GUIDE WIRE HOLDER

Exemplary embodiments relates to a guide wire holder and a method for inserting the same. This application is a continuation application based on International Patent Application No. PCT/JP2019/001430 filed on Jan. 18, 2019 and International Patent Application No. PCT/JP 2018/027283 filed on Jul. 20, 2018, and the contents of the PCT international applications are incorporated herein by reference.

BACKGROUND

A method of introducing a medical device into a hollow organ of the human body using a guide wire during a treatment or an examination of the hollow organ is known (for example, Japanese Unexamined Patent Application, First Publication No. 2016-140630). In this method, the guide wire may not be able to be inserted into the hollow organ when an opening portion of the hollow organ has an obstacle such as a stenosis or occlusion. For example, when the duodenal papilla is occluded, it is difficult to insert a guide wire into a target hollow organ such as the bile duct or pancreatic duct via the duodenal papilla.

A method called a rendezvous method is known as a coping method in such a case. In the rendezvous method, a guide wire introduced into the bile duct or pancreatic duct from a region other than the duodenal papilla protrudes from the duodenal papilla, and an end portion of the protruding guide wire is held by a medical device. The guide wire protruding from the duodenal papilla is pulled out of the body via a treatment tool channel of an endoscope inserted into the duodenum. A stent or the like is placed using the guide wire pulled out of the body.

For example, Japanese Unexamined Patent Application, First Publication No. 2016-140630 discloses a medical device which can capture a guide wire protruding from the duodenal papilla. The medical device includes a tubular sheath, a wire inserted through the sheath, and a distal end portion provided at a distal end of the wire and extending in an extending direction of the wire. The distal end portion has a bent portion which is bent into a predetermined shape so that the guide wire is capable of being hooked.

Further, for example, as described in United States Patent Application Publication No. 2016-0121083, a method is known in which, when a treatment tool such as a stent is placed by the rendezvous method, a guide wire protruding from the duodenal papilla into the duodenum is pulled back into the bile duct or pancreatic duct and thus a medical device gripping the guide wire is introduced into the bile duct or pancreatic duct together with the treatment tool.

In the rendezvous method, the bile duct or pancreas is observed on an ultrasound image, and a puncture needle punctures an intrahepatic bile duct or an extrahepatic bile duct from the esophagus, stomach, and duodenum. A guide wire is inserted inside the puncture needle that has punctured the bile duct, and a distal end of the guide wire is inserted inside the bile duct or the pancreatic duct. Then, the guide wire is pushed forward to pass through the duodenal papilla, and the distal end side portion of the guide wire is caused to protrude into the duodenum. Then, while the distal end side portion of the guide wire protruding from the papilla of the duodenum is observed on an endoscopic image, a part of the distal end side portion of the guide wire is gripped by a grip portion of a treatment tool (for example, a gripping forceps). The treatment tool is drawn into the papilla by pulling the guide wire in this state. Accordingly, for example, the treatment tool placed in the bile duct is capable of being placed in the bile duct in a state in which the treatment tool is covered with an indwelling object such as a stent, instead of a guide sheath.

Treatment tools for realizing a procedure disclosed in Japanese Unexamined Patent Application, First Publication No. 2016-140630 and United States Patent Application Publication No. 2016-0121083 have been studied (for example, Japanese Unexamined Patent Application, First Publication No. 2017-169783). The device of Japanese Unexamined Patent Application, First Publication No. 2017-169783 captures the guide wire and inserts it into the duodenal papilla side along the guide wire to insert the treatment tool into the bile duct while minimizing damage to the papillary tissue. Specifically, the device of Japanese Unexamined Patent Application, First Publication No. 2017-169783 has a constitution in which a cutout portion is provided at a distal end portion of a sheath and a guide wire is held in the cutout portion. The endoscope catheter has a constitution in which the guide wire is inserted into the cutout portion by pressing an opening of the cutout portion from the side diagonally outward therefrom against the guide wire, and the sheath is slid along the guide wire in this state.

SUMMARY

A guide wire holder can include a sheath having a lumen of which a central axis extends along a longitudinal axis, an operation wire which is inserted through the lumen to be able to advance and retract along the longitudinal axis, and a hook which is continuous with a distal end of the operation wire and protrudes from a distal end of the sheath, wherein the sheath has an inner wall surface which forms a groove configured to extend from the distal end of the sheath to a proximal end side of the sheath, the groove has an opening portion which opens on an outer peripheral surface of the sheath, the hook has a guide wire engagement surface which is engageable with a guide wire, and the guide wire engagement surface and the inner wall surface are configured to be capable of holding the guide wire in a state in which the guide wire engagement surface is located closer to a distal side than the groove.

DETAILED DESCRIPTION OF EXEMPLARY EMBODIMENTS

First Embodiment

Hereinafter, a first embodiment of a guide wire holder according to the present invention will be described with reference to FIGS. 1 to 12.

Figure 1:
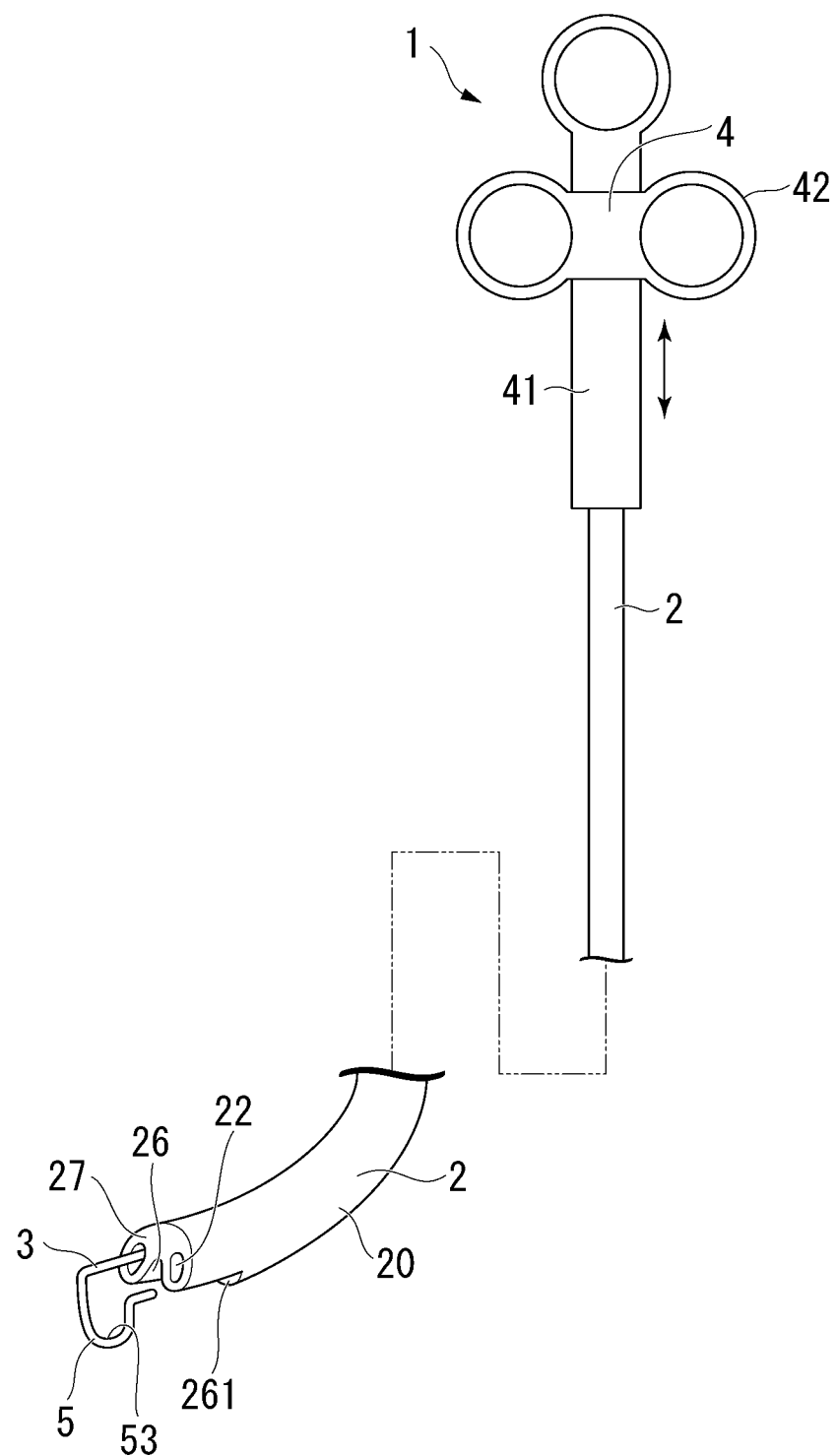
FIG. 1 is an overall view showing a guide wire holder according to an exemplary embodiment.
Figure 2:
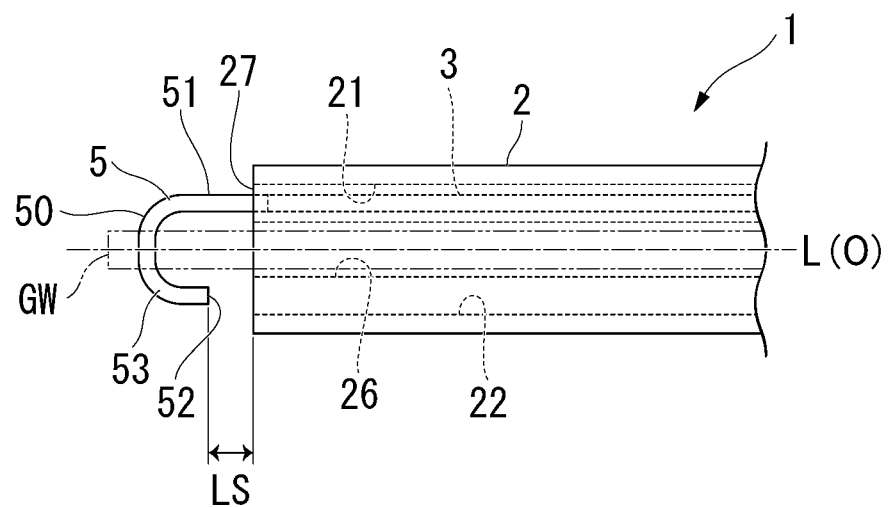
FIG. 2 is a top view showing a distal end portion of the guide wire holder according to an exemplary embodiment.
Figure 3:
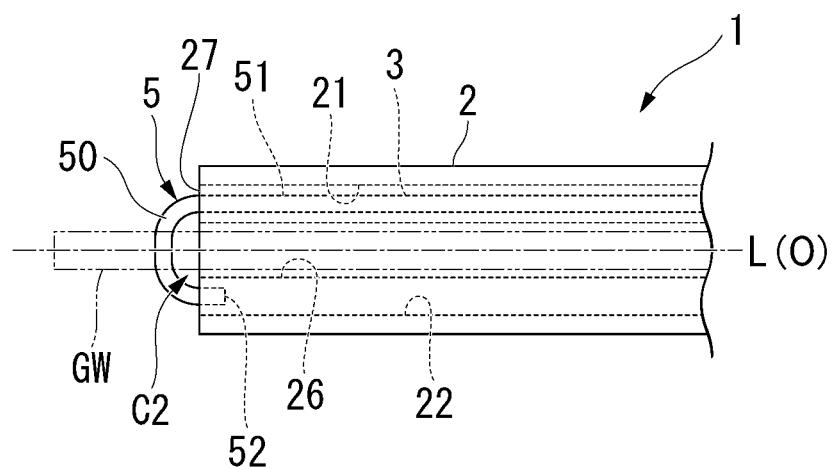
FIG. 3 is a top view showing a distal end portion of the guide wire holder according to an exemplary embodiment.
Figure 4:
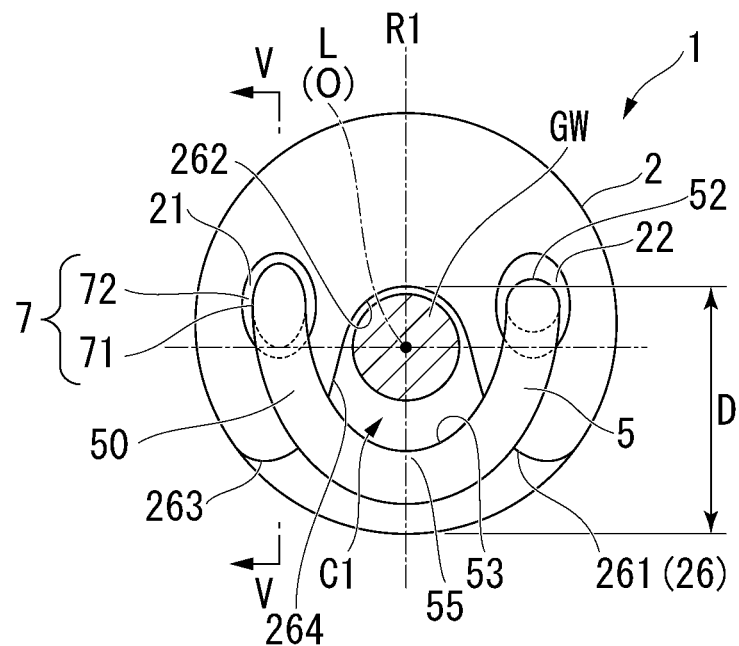
FIG. 4 is a front view of the guide wire holder according to an exemplary embodiment from the distal side.
Figure 5:
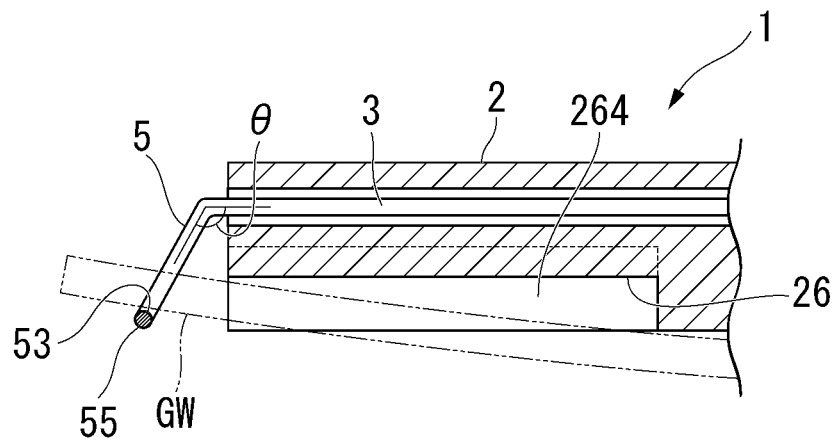
FIG. 5 is a cross-sectional view along line V-V shown in FIG. 4.
Figure 6:
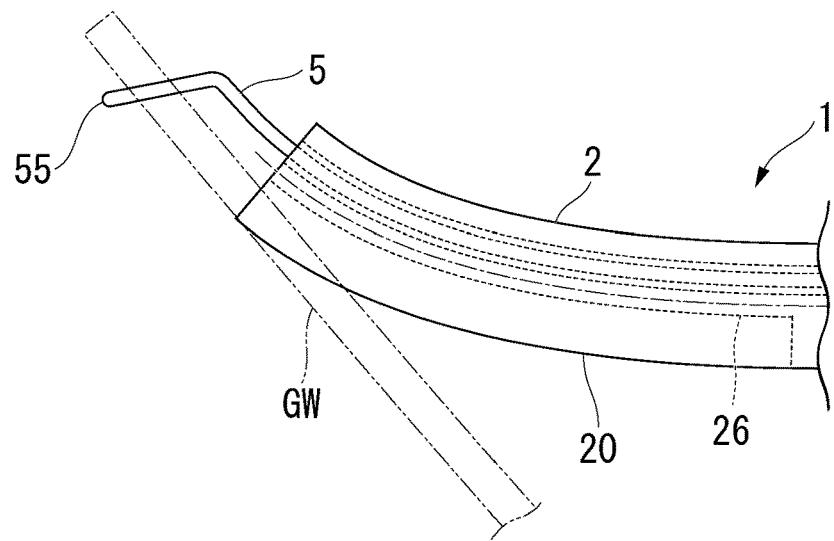
FIG. 6 is a side view showing an aspect of a pre-curved portion of the guide wire holder according to an exemplary embodiment.
Figure 7:
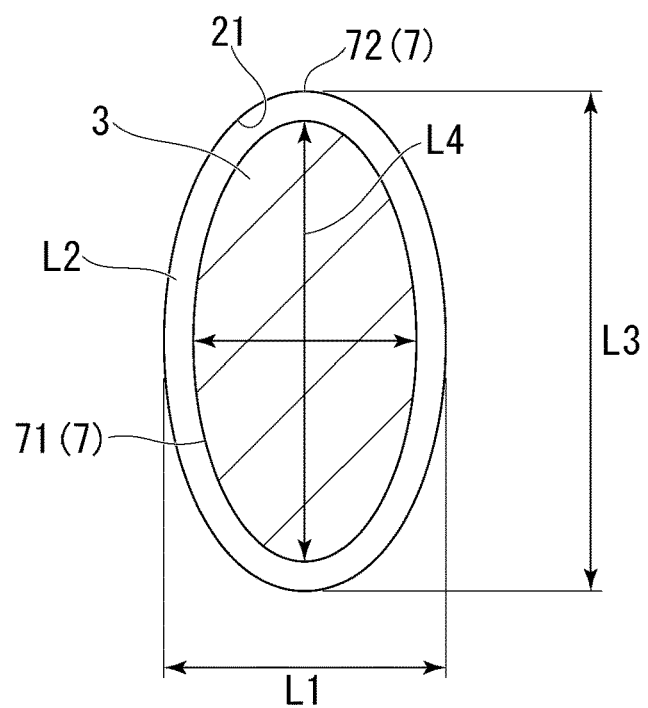
FIG. 7 is a schematic view showing a rotation-preventing structure of the guide wire holder according to an exemplary embodiment.

FIG. 1 is an overall view showing a guide wire holder 1 according to the embodiment. FIG. 2 is a top view showing a distal end portion of the guide wire holder 1. FIG. 3 is a top view showing the distal end portion of the guide wire holder 1 and is a view showing a state in which a hook shown in FIG. 2 is retracted. FIG. 4 is a front view of the guide wire holder 1 when seen from the distal end side. FIG. 5 is a cross-sectional view along line V-V shown in FIG. 4. FIG. 6 is a side view showing an aspect when the guide wire holder 1 is used. FIG. 7 is a view schematically showing a rotation-preventing portion 7 of the guide wire holder 1.

The guide wire holder 1 according to the embodiment is a medical device which is capable of holding a wire, for example, a medical guide wire that is inserted into the body when used. The guide wire holder 1 is a treatment tool constituted such that a hook 5 advances and retracts on the distal side of a sheath 2 as an operation wire 3 advances and retracts, and the guide wire located outside the sheath 2 is capable of being captured and held by the hook 5. As shown in FIGS. 1 and 2, the guide wire holder 1 includes the sheath 2, the operation wire 3, the hook 5, and an operation portion 4.

The sheath 2 is a long flexible member. A proximal end portion of the sheath 2 is connected to an operation portion main body 41 of the operation portion 4 which is gripped by an operator. The sheath 2 is inserted into the body through an endoscope insertion portion and has such a length that a distal end portion of the sheath is capable of protruding from the endoscope. As shown in FIGS. 2 to 4, the sheath 2 has a first lumen 21 (a lumen) which extends in a direction of a longitudinal axis L. Further, the sheath 2 has a second lumen (a hook-accommodating lumen) 22 which extends parallel to the first lumen 21. In a front view of the distal end of the sheath 2 seen in a direction along the longitudinal axis L of the sheath 2, the first lumen 21 and the second lumen 22 are formed on both sides of a first diameter line R1 which is a straight line passing through a central axis O of the sheath 2 and orthogonal to the central axis O. The second lumen 22 has an inner diameter larger than an outer diameter of a second end portion 52.

In FIG. 4, although the longitudinal axis L and the central axis O are shown by the same line, the central axis O is an axis which passes through a center of the sheath 2 in a substantially circular cross-sectional shape, and the longitudinal axis L is an axis which extends in a longitudinal direction of the sheath 2.

As shown in FIGS. 1 and 4, a groove 26 is formed in a part of an outer periphery of the sheath 2. The groove 26 is formed in a concave shape at a part of an outer periphery of the sheath 2. The groove 26 is formed to extend from the distal end of the sheath 2 toward the proximal side in the direction of the longitudinal axis L. As shown in FIG. 4, the groove 26 is formed so that a part of the outer periphery of the sheath 2 is recessed from an outer peripheral surface toward the central axis O. The groove 26 has a depth D which is longer than a radius of the sheath 2. In the groove 26, at least at the distal end of the sheath 2, as shown in FIG. 4, in a front view, the groove 26 includes a bottom portion 262 located between the first lumen 21 and the second lumen 22, and a distal end edge (a ridge line) 261 formed in a curved shape in which an opening width of the groove 26 widens from the bottom portion 262 toward the outer peripheral surface of the sheath 2. The bottom portion 262 of the groove 26 is formed in an arc shape in a cross section orthogonal to the central axis O. An edge portion of the groove 26 on an outer peripheral opening portion 263 side (an opening side of the groove) on the outer peripheral side of the sheath 2 is formed in a curved shape and has a curved surface. The groove 26 opens on a first diameter line R1. The groove 26 does not necessarily have to have the depth D longer than the radius of the sheath 2 and may have a depth shorter than the radius of the sheath 2.

The groove 26 is formed to extend from the distal end of the sheath 2 toward the proximal side in the direction of the longitudinal axis L. The groove 26 has the same shape as the distal end edge 261 from a distal end of the groove 26 to the proximal end of the groove. The groove 26 may be formed over the entire length of the sheath 2 or may be formed in a region of a predetermined length from the distal end toward the proximal side, for example, only in a portion which protrudes from a distal end of the endoscope insertion portion.

As shown in FIGS. 1 and 6, a pre-curved portion 20 is provided at the distal end portion of the sheath 2. The pre-curved portion 20 has a curved shape which has a bending tendency in a predetermined direction. In the embodiment, the pre-curved portion 20 has a curved shape which is curved to be bent in a direction of the first diameter line R1. The pre-curved portion 20 is elastically deformed when an external force is applied, but in a natural state in which the external force is released, the pre-curved portion 20 has a restoring force which restores the curved shape given in advance. The groove 26 is formed at a position at which it opens outside the curved shape of the pre-curved portion 20 when the pre-curved portion 20 is restored to the curved shape.

The operation wire 3 is formed of a single wire or a stranded wire made of a metal and is inserted through the first lumen 21 of the sheath 2. A proximal end of the operation wire 3 is fixed to an operation slider 42 of the operation portion 4, and the hook 5 is connected to a distal end of the operation wire 3.

A rotation-preventing portion 7 is provided in the operation wire 3 and the first lumen 21. The rotation-preventing portion 7 prevents the operation wire 3 from rotating about the axis with respect to the first lumen 21. The rotation-preventing portion 7 includes a non-round portion 71 (a restricted portion) provided in the operation wire 3 and a non-round opening portion 72 (a restricting portion) provided in the first lumen 21. The non-round portion 71 is a portion of which a cross-sectional shape orthogonal to an axial direction of the operation wire 3 is elliptical (non-round). The non-round opening portion 72 is an elliptical opening which has an elliptical (non-round) opening shape and is provided to have a predetermined length from the distal end of the first lumen 21 toward the proximal side and of which a cross-sectional shape thereof orthogonal to the direction of the longitudinal axis L of the sheath 2 is similar to that of the non-round portion 71 of the operation wire 3. As shown in FIG. 7, the non-round opening portion 72 has an opening size which allows the operation wire 3 to advance and retract and in which the non-round portion 71 cannot rotate about the axis of the operation wire 3. The restricting portion and the restricted portion may have a non-round shape and may have an elliptical shape or an oval shape.

As shown in FIG. 7, a dimension L1 of the non-round opening portion 72 in a short side direction of the elliptical shape is larger than a dimension L2 of a cross section of the non-round portion 71 in a short side direction thereof. A dimension L3 of the non-round opening portion 72 in a long side direction of the elliptical shape is larger than the dimension L1 of the non-round portion 71 in the short side direction and a dimension L4 thereof in the long side direction. Therefore, when the operation wire 3 rotates about its own axis, the non-round portion 71 comes into contact with an inner wall of the non-round opening portion 72, and rotation of the operation wire 3 about the axis is restricted. As a result, the operation wire 3 is constituted to be able to advance and retract in the first lumen 21 while the operation wire 3 is prevented from rotating about the axis with respect to the sheath 2.

The non-round portion 71 of the operation wire 3 is provided in a region at which the operation wire 3 passes through the non-round opening portion 72 of the distal end portion of the first lumen 21 when the operation wire 3 advances and retracts with respect to the sheath 2. In the embodiment, in the operation wire 3, the elliptical non-round portion 71 is provided in a part of the operation wire 3 in the longitudinal direction, and a cross-sectional shape of a portion other than the non-round portion 71 is substantially completely circular.

As shown in FIGS. 1 to 3, the hook 5 is provided to be continuous with the distal end of the operation wire 3. The hook 5 is formed by bending a wire-shaped member toward the distal end side of the guide wire holder 1 in a convex shape. The hook 5 includes a first end portion 51 which has end portions on both sides of a convex bending region 50 and is connected to the distal end of the operation wire 3, and a second end portion 52 which extends toward the proximal end side of the sheath 2 along the longitudinal axis. The hook 5 may be formed of a single wire made of a metal such as SUS or a nickel titanium alloy.

The hook 5 is provided to protrude from the distal end of the sheath 2. The hook 5 advances and retracts at the distal side of the sheath 2 as the operation wire 3 advances and retracts with respect to the sheath 2.

As shown in FIGS. 4 and 5, in a front view, the hook 5 is formed to be bent in a radial direction (a direction of the first diameter line R1) of the sheath 2 and to the side on which the groove 26 is located. In a side view in a direction orthogonal to the direction of the longitudinal axis L of the sheath 2 and a direction orthogonal to a bending direction of the pre-curved portion 20, the hook 5 is bent so that the distal end side of the hook 5 is bent toward the groove 26 side at a right angle or an obtuse angle with the distal end part of the guide wire. As shown in FIG. 4, in a front view, a protruding end portion 55 of the curved portion at the distal end of the hook 5 is located outward from the bottom portion 262 of the groove 26 in the radial direction of the sheath 2. That is, the hook 5 is bent toward the groove 26 in the direction of the first diameter line R1 between the first end portion 51 and the second end portion 52 and the protruding end portion 55. An inner surface of the curved portion of the protruding end portion 55 serves as a guide wire engagement surface 53 which is capable of engaging with the guide wire. Here, the engagement means that the hook hooks the guide wire, and is used regardless of whether the guide wire can advance and retract with respect to the hook.

In a front view, the hook 5 intersects the distal end edge 261 of the groove 26, and a closed region C1 closed by the hook 5 and the distal end edge 261 is formed. As shown in FIG. 3, in a first side view (a top view) along the first diameter line R1, when the hook 5 is disposed at a retracted position, the second end portion 52 is accommodated in the distal end of the sheath 2 to form a closed region C2 between the hook 5 and the distal end of the sheath 2.

As shown in FIG. 1, the operation portion 4 is provided on the proximal end side of the guide wire holder 1 and is connected to the proximal end of the sheath 2. The operation portion 4 includes an operation portion main body 41 and the operation slider 42. The operation portion main body 41 is connected to the proximal end of the sheath 2. The operation slider 42 is slidably mounted on the operation portion main body 41. The operation portion main body 41 has a hollow portion, and a slit (not shown) which is allowed to communicate with the hollow portion and the outside and extends along the longitudinal axis L is formed. A part of the operation slider 42 is inserted through the slit, and the operation slider 42 is connected to the proximal end portion of the operation wire 3 in the hollow portion. When the operation slider 42 is advanced and retracted with respect to the operation portion main body 41 in the direction of the longitudinal axis L of the sheath 2, the operation wire 3 advances and retracts with respect to the sheath 2, and the hook 5 is capable of advancing and retracting on the distal end side of the sheath 2 according to the advancing and retracting of the operation wire 3.

When the operation slider 42 is advanced with respect to the operation portion main body 41, the operation wire 3 advances in the first lumen 21, and the hook 5 advances on the distal side of the sheath 2. When the operation slider 42 is advanced furthest to the distal side in a movable range of the operation slider 42, the hook 5 is disposed at the most advanced position with respect to the sheath 2. As shown in FIG. 2, the second end portion 52 of the hook 5 is separated from the distal end of the sheath 2 in the advanced position. Specifically, a separation distance LS (refer to FIG. 2) between the second end portion 52 and the distal end of the sheath 2 in the advanced position is longer than a diameter of a guide wire GW which will be described later.

The second end portion 52 is capable of being accommodated in the second lumen 22 by retracting the operation wire 3. When the operation slider 42 is retracted furthest to the proximal side in the movable range of the operation slider 42, as shown in FIG. 3, the hook 5 is disposed at the most retracted position with respect to the sheath 2, and the second end portion 52 enters a distal end opening of the second lumen 22 and is accommodated therein.

Since the rotation of the operation wire 3 around the axis is prevented by the rotation-preventing portion 7, the hook 5 advances and retracts while a relative position around the axis with respect to the central axis O of the sheath 2 is maintained. Therefore, the second end portion 52 is capable of reliably entering the distal end opening of the second lumen 22 at the retracted position of the hook 5.

Figure 8:
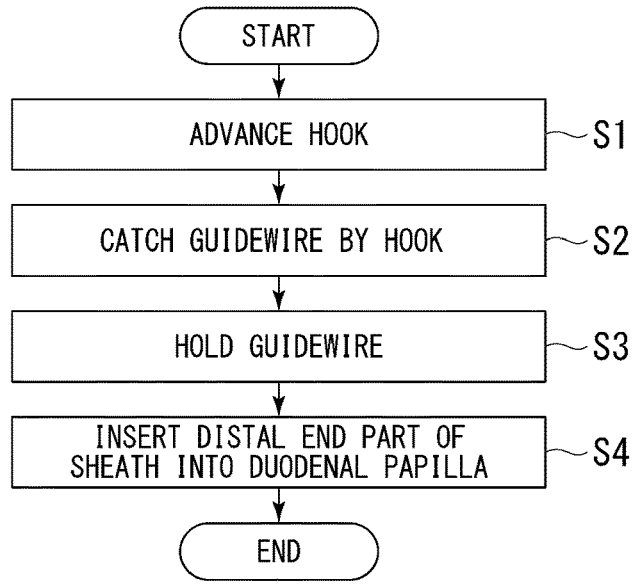
FIG. 8 is a flowchart showing a method for inserting the guide wire holder according to an exemplary embodiment.
Figure 9:
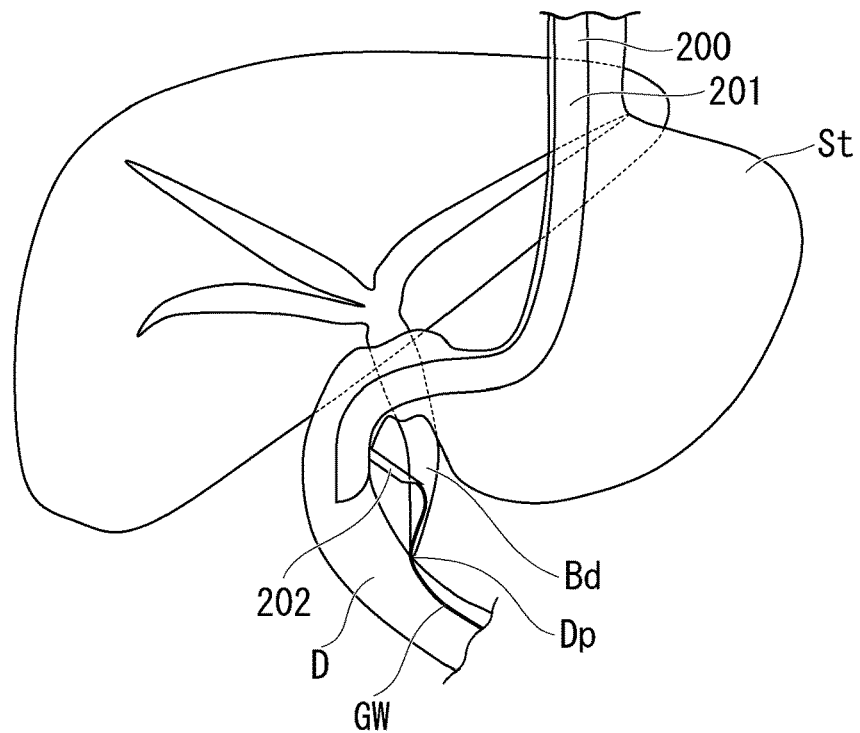
FIG. 9 is a schematic view showing an aspect when the guide wire holder according to an exemplary embodiment is used.
Figure 10:
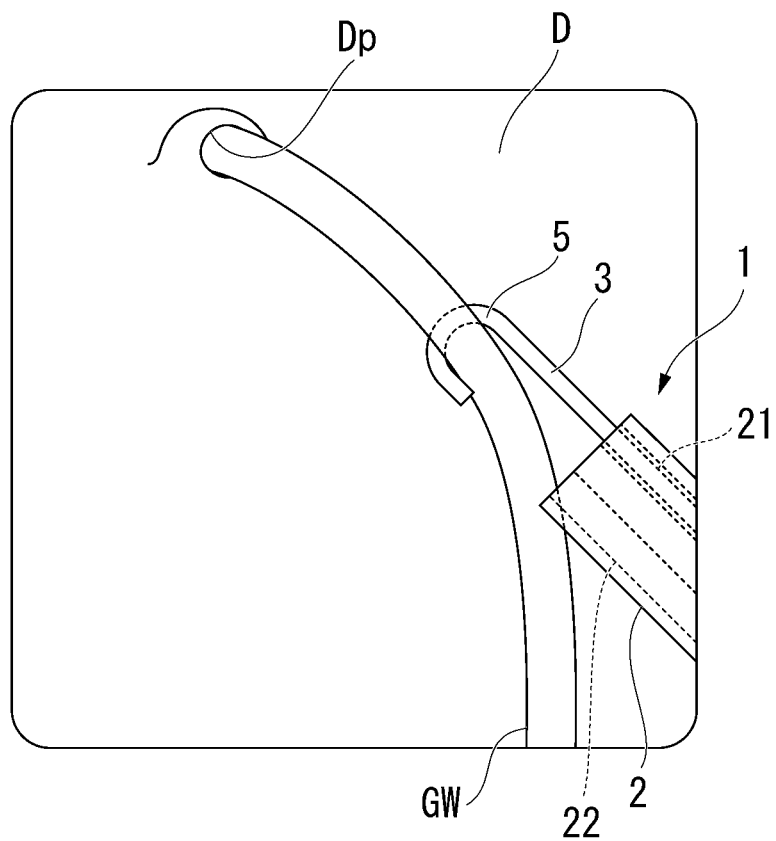
FIG. 10 is a schematic view showing an endoscopic image in an example in which a procedure is performed by a rendezvous method using the guide wire holder according to an exemplary embodiment.
Figure 11:
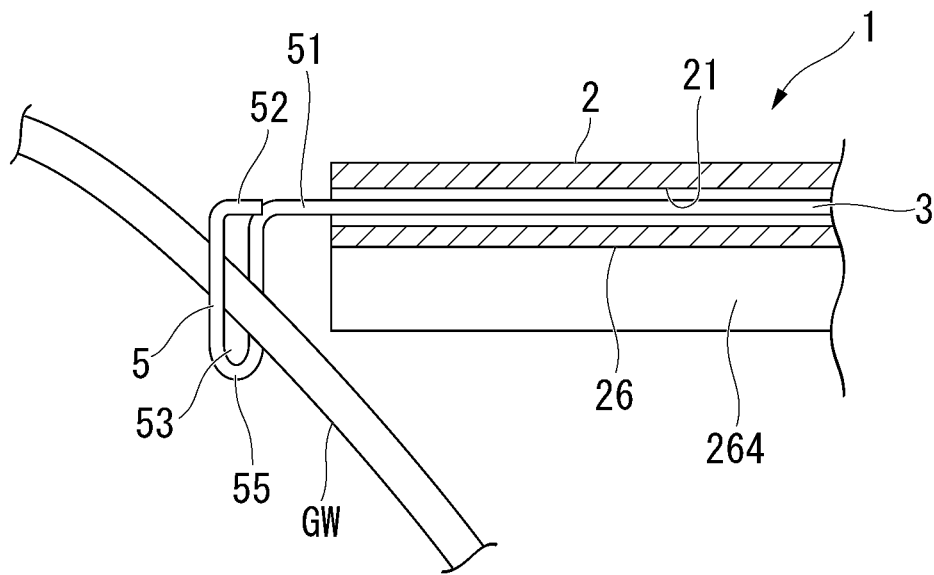
FIG. 11 is a schematic view showing an aspect when the guide wire holder according to an exemplary embodiment is used.
Figure 12:
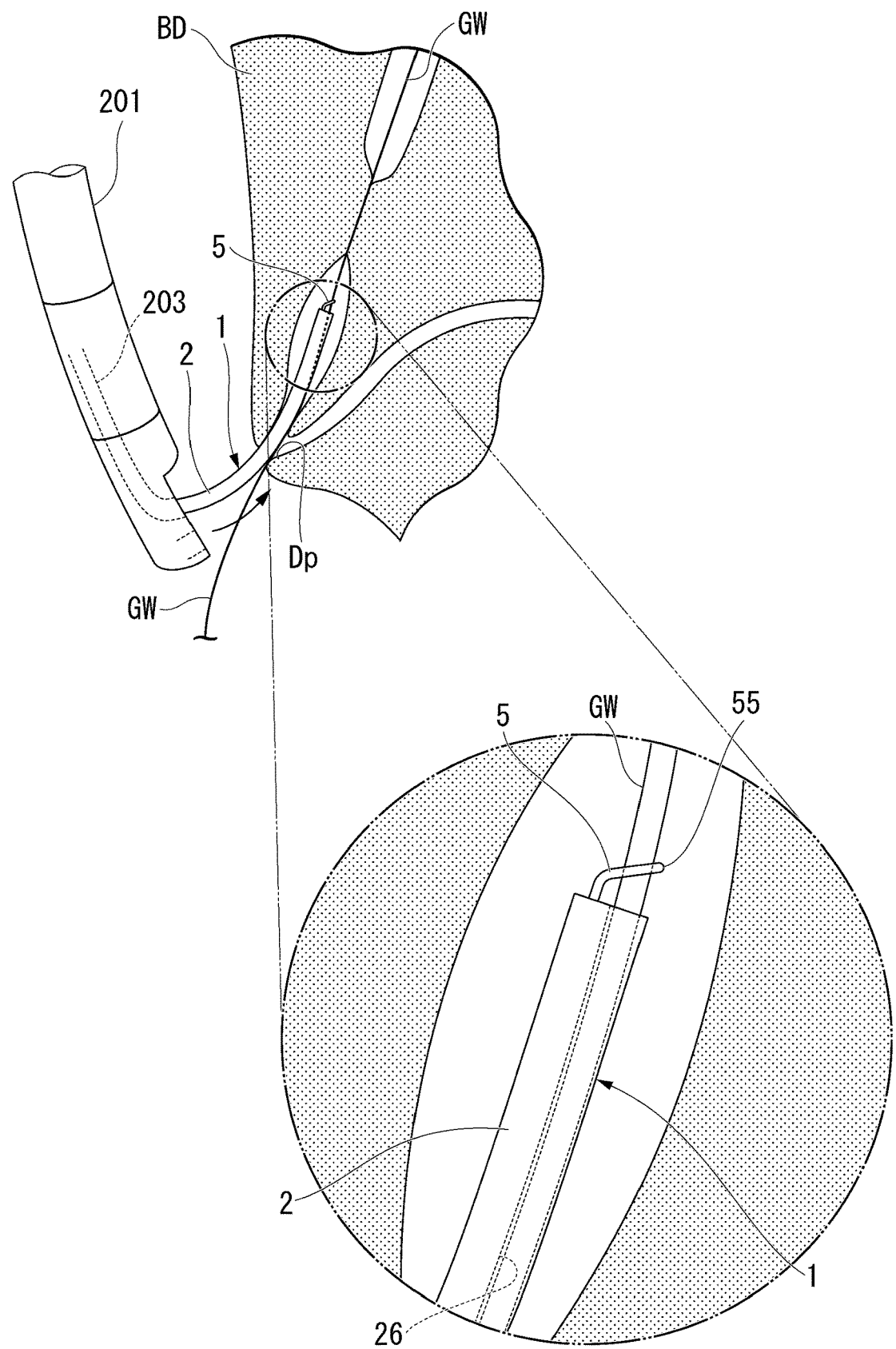
FIG. 12 is a schematic view showing an endoscopic image in an example in which a procedure is performed by a rendezvous method using the guide wire holder according to an exemplary embodiment.

Next, a usage aspect of the guide wire holder 1 and a method for inserting the guide wire holder will be described. In the following, a method for introducing the guide wire holder 1 into a hollow organ, for example, the bile duct, by the rendezvous method will be described as an example. FIG. 8 is a flowchart showing the method for inserting the guide wire holder according to the embodiment. FIGS. 9 to 11 are schematic views showing an aspect when the guide wire holder 1 is used. FIG. 12 is a schematic view showing an example in which a procedure is performed by the rendezvous method using the guide wire holder 1.

First, a first guide wire GW (the guide wire) is placed in a duodenum D. Specifically, as shown in FIG. 9, an endoscope insertion portion 201 of an ultrasonic endoscope 200 is inserted from the mouth of a patient into the stomach St or the duodenum D, and an access needle 202 which is inserted through the endoscope insertion portion 201 and protrudes from the distal end of the endoscope insertion portion 201 punctures the bile duct Bd. Then, the first guide wire GW is inserted into the endoscope insertion portion 201, and the first guide wire GW is inserted into the bile duct Bd via the access needle 202. The first guide wire GW inserted into the bile duct Bd is pushed forward, and the distal end of the first guide wire GW protrudes from the duodenal papilla Dp into the duodenum D. Normally, the distal end of the first guide wire GW which protrudes from the duodenal papilla Dp is made to extend along the lumen of the duodenum D by advancing the first guide wire GW toward the duodenal papilla Dp. After that, the ultrasonic endoscope 200 is removed with the first guide wire GW left inside the body, and the distal end of the first guide wire GW is placed in the duodenum D. At this time, a proximal end part of the first guide wire GW is outside the patient's body.

Next, the endoscope insertion portion 201 (refer to FIG. 12) of a duodenoscope (not shown) is inserted from the patient's mouth to the duodenum D. Then, the guide wire holder 1 is inserted into the endoscope insertion portion 201, and the distal end portion of the sheath 2 protrudes from the distal end of the endoscope insertion portion 201. At this time, the distal end portion of the sheath 2 is raised by an elevator (not shown) provided at a distal end portion of a treatment tool channel 203 of the endoscope insertion portion 201. When the distal end portion of the sheath 2 protrudes from the treatment tool channel 203 of the endoscope insertion portion 201, the pre-curved portion 20 is restored to a predetermined curved shape. Therefore, the distal end portion of the sheath 2 is capable of being easily arranged to be displayed in an endoscopic image, and the sheath 2 is also capable of being guided in a direction in which the hook 5 easily hooks the guide wire GW. The guide wire GW is capable of being easily inserted into the groove 26. Since the second end portion 52 of the hook 5 is located in the central part of the endoscopic image, the second end portion 52 is capable of being seen closer to a center of the endoscopic image than the first guide wire GW. As a result, in the endoscopic image, a gap between the second end portion 52 and the sheath 2 is prevented from being blocked by the first guide wire GW, and the hook 5 is capable of smoothly hooking the first guide wire GW.

As shown in FIG. 10, an operator operates the operation portion 4 while checking the endoscopic image obtained by the duodenoscope. Specifically, the endoscope insertion portion 201 is disposed so that the first guide wire GW which protrudes from the duodenal papilla Dp toward the inside of the duodenum D is displayed in the endoscopic image, and in this state, the sheath 2 protrudes from the endoscope insertion portion 201 to bring the sheath 2 close to the first guide wire GW. As shown in FIG. 10, the distal end portion of the sheath 2 is imaged to protrude from the lower right side of the endoscopic image and is reflected therein. When the sheath 2 is caused to protrude from the endoscope, the sheath 2 is disposed at a position at which the gap between the second end portion 52 of the hook 5 and the distal end of the sheath 2 is capable of being visible in the endoscopic image. That is, the second end portion 52 is displayed closer to the proximal side than the first end portion 51 in the endoscopic image.

Then, the operation slider 42 is advanced toward the distal side, the operation wire 3 is advanced with respect to the sheath 2, and the hook 5 is advanced to the advanced position with respect to the sheath 2 (a hook advance step S1).

As shown in FIGS. 10 and 11, the operator inserts the first guide wire GW into the gap between the second end portion 52 of the hook 5 and the distal end of the sheath 2 while checking the endoscopic image. Then, the first guide wire GW is hooked by the hook 5 (a locking step S2).

The guide wire GW which protrudes from the duodenal papilla Dp runs from the upper side to the lower side in the endoscopic image, and the vicinity of the distal end of the endoscope is displayed on the lower side of the endoscopic image. On the other hand, when the pre-curved portion 20 passes through a forceps-elevator 100, the outside of the curve of the pre-curved portion 20 faces the forceps-elevator 100 (refer to FIG. 25). Therefore, since the groove 26 is formed on the outside of the curve of the pre-curved portion 20, the groove 26 is located below the endoscopic image when the pre-curved portion 20 protrudes from the endoscope. As a result, it becomes easy to accommodate the guide wire GW in the groove 26 of the sheath 2. Since a vector of a force pushing the sheath 2 is easily converted in a long axis direction of the guide wire GW, the distal end portion of the sheath 2 is likely to follow the guide wire GW.

Next, the operator retracts the operation slider 42 toward the proximal side, retracts the operation wire 3 with respect to the sheath 2 and places the hook 5 in the retracted position. The first guide wire GW is capable of being brought close to the distal end edge of the groove 26 by retracting the hook 5 to the retracted position. In the retracted position, the second end portion 52 of the hook 5 is inserted into the second lumen 22, and the first guide wire GW is disposed and captured in the closed regions C1 and C2 between the hook 5 and the sheath 2 (a guide wire-holding step S3).

In the state in which the hook 5 is retracted to the retracted position, the guide wire GW is guided by the guide wire engagement surface 53 and inserted into the groove 26. In the retracted position, the guide wire engagement surface 53 of the hook 5 is located closer to the distal side than a distal end of the outer peripheral opening portion 263 (the opening portion) of the groove 26. At this time, the guide wire GW is captured and held by an inner wall surface 264 of the groove 26 and the guide wire engagement surface 53 of the hook 5 in a state in which the guide wire GW is arranged from the groove 26 toward the proximal end side of the sheath 2 along the direction of the longitudinal axis L. The guide wire GW is preferably held between the guide wire engagement surface 53 of the hook 5 and the inner wall surface 264 of the groove 26 to be able to advance and retract. The guide wire GW is capable of being prevented from coming off from the guide wire holder 1 by holding the guide wire GW between the guide wire engagement surface 53 of the hook 5 and the inner wall surface 264 of the groove 26.

Next, in a state in which the guide wire GW is held between the hook 5 and the groove 26, the distal end portion of the sheath 2 is inserted into the duodenal papilla Dp along the guide wire GW while the inner wall surface 264 of the groove 26 is pressed against the guide wire GW (a sheath insertion step S4). The operator pushes the operation portion 4 and inserts the distal end portion of the sheath 2 into the duodenal papilla Dp as shown in FIG. 12. Since the first guide wire GW passes through the bile duct Bd and extends to the duodenum D via the duodenal papilla Dp in advance, when the guide wire holder 1 is pushed in, the sheath 2 advances along the first guide wire GW and reaches the inside of the bile duct Bd.

Since the closed regions C1 and C2 are sufficiently larger than the diameter of the first guide wire GW, the sheath 2 and the hook 5 do not generate a large frictional resistance with the first guide wire GW. Therefore, the sheath 2 is capable of being smoothly advanced and retracted along the first guide wire GW. Further, when the sheath 2 is advanced into the duodenal papilla Dp, the first guide wire GW is disposed in the groove 26 of the sheath 2 in the direction of the longitudinal axis L of the sheath 2, and the guide wire GW is also held between the hook 5 and the groove 26. As a result, a state in which the first guide wire GW is disposed along the longitudinal axis L of the sheath 2 is maintained. At this time, at least a part of the hook 5 is located distant from the distal end of the groove 26. Further, the first guide wire GW is held along the longitudinal axis L at a position closer to the central axis O of the sheath 2, and as described above, the sheath 2 and the hook 5 smoothly advance and retract with respect to the first guide wire GW. Therefore, the sheath 2 and the hook 5 is capable of being easily inserted into the bile duct Bd. In this way, the insertion of the first guide wire GW into the bile duct Bd is completed.

After the insertion of the first guide wire GW into the bile duct Bd is completed, an intended treatment is performed. As a specific example, a second guide wire different from the first guide wire GW is inserted into another lumen (not shown) of the sheath 2 or the second lumen 22, and the second guide wire is inserted into the duodenal papilla Dp. Then, the first guide wire GW and the guide wire holder 1 are removed from the endoscope insertion portion 201.

After that, another endoscopic treatment tool is inserted into the duodenoscope and is inserted into the duodenum along the second guide wire, and then a treatment in the duodenum is performed. Examples of treatments performed by another endoscopic treatment tool include injection of a contrast medium, calculus removal, and a placement of a stent, and the like.

According to the guide wire holder 1 of the embodiment, since the hook 5 which protrudes from the distal end of the sheath 2 and is capable of advancing and retracting with respect to the sheath 2 is provided, the guide wire GW is capable of being held by the hook 5. According to the guide wire holder 1 of the embodiment, the guide wire GW is capable of being easily hooked by the hook 5 by disposing the hook 5 at the advanced position. When the guide wire GW is hooked by the hook 5, the gap formed between the second end portion 52 and the distal end of the sheath 2 is capable of being visually recognized in the endoscopic image, and thus the guide wire GW is easily hooked by the hook 5. Since the separation distance LS between the second end portion 52 and the distal end of the sheath 2 at the advanced position of the hook 5 is larger than the outer diameter of the guide wire GW, the guide wire GW is capable of being easily hooked by the hook 5. Then, the guide wire GW is capable of being prevented from coming off from the hook 5 by disposing the hook 5 at the retracted position.

Since the closed regions C1 and C2 formed by the guide wire engagement surface 53 of the hook 5 and the distal end edge (the ridge line) 261 of the distal end of the groove 26 of the sheath 2 are larger than the outer diameter of the guide wire GW, the guide wire GW captured in the closed regions C1 and C2 are capable of smoothly advancing and retracting in the closed regions C1 and C2. As a result, when the distal end portion of the guide wire holder 1 is inserted into the duodenum, the sheath 2 is capable of being easily advanced along the guide wire GW.

According to the guide wire holder 1 of the embodiment, the rotation of the operation wire 3 around its own axis is restricted by the rotation-preventing portion 7. As a result, when the hook 5 advances and retracts, the second end portion 52 of the hook 5 is prevented from rotating around the central axis O of the sheath 2, and the second end portion 52 is capable of being reliably inserted into the second lumen 22 when the hook 5 retracts.

Since the guide wire holder 1 according to the embodiment includes the groove 26 formed along the longitudinal axis L on the outer periphery of the sheath 2, when the inner wall surface 264 of the groove 26 is pressed against the guide wire GW located outside the sheath 2, the guide wire GW is capable of being easily inserted into the groove 26.

According to the guide wire holder 1 of the embodiment, in a front view seen in the direction along the longitudinal axis L, the hook 5 intersects the distal end edge 261 of the groove 26, and the closed region C1 closed by the hook 5 and the distal end edge 261 is formed. Therefore, in a state in which the hook 5 is disposed at the retracted position, the guide wire GW located outside the sheath 2 is capable of being captured in the groove 26 and held in the closed region C1. As a result, the guide wire GW is capable of being easily hooked by the hook 5 by the advancing and retracting operation of the operation wire 3, and the guide wire GW is capable of being surrounded and held between the guide wire engagement surface 53 of the hook 5 and the distal end edge 261 of the groove 26. Therefore, when the sheath 2 is inserted into the duodenal papilla Dp, the hook 5 does not come off from the guide wire GW, and the sheath 2 is capable of being inserted into the duodenal papilla Dp in a stable state.

According to the guide wire holder 1 of the embodiment, since the guide wire GW is inserted and held in the groove 26, the guide wire GW is capable of being held near the central axis O of the sheath 2. Therefore, the guide wire GW is capable of being held by a simple operation, and the sheath 2 is capable of being smoothly advanced along the guide wire GW in the hollow organ. Furthermore, since the guide wire GW is captured and held along the groove 26, when the sheath 2 is inserted into the duodenal papilla Dp, a diameter of a portion including the sheath 2 and the guide wire GW is capable of being curbed, and the sheath 2 is capable of being easily inserted into the duodenal papilla Dp.

Since the guide wire holder 1 according to the embodiment includes the pre-curved portion 20 in the sheath 2, and the groove 26 is formed to open outside a restored curved shape of the pre-curved portion 20, the guide wire GW is capable of being easily inserted into the groove 26. Also, the pre-curved portion 20 is not an essential component, and the guide wire holder 1 is capable of smoothly inserting the guide wire GW into the groove 26 even when the sheath 2 does not include the pre-curved portion 20.

The guide wire holder according to the present invention is not limited to the example of the above-described embodiment. For example, modified examples shown in FIGS. 13 to 29 can be cited. In the following description, the same components as those already described will be designated by the same reference numerals, and duplicate description thereof will be omitted.

First Modified Example of First Embodiment

Figure 13:
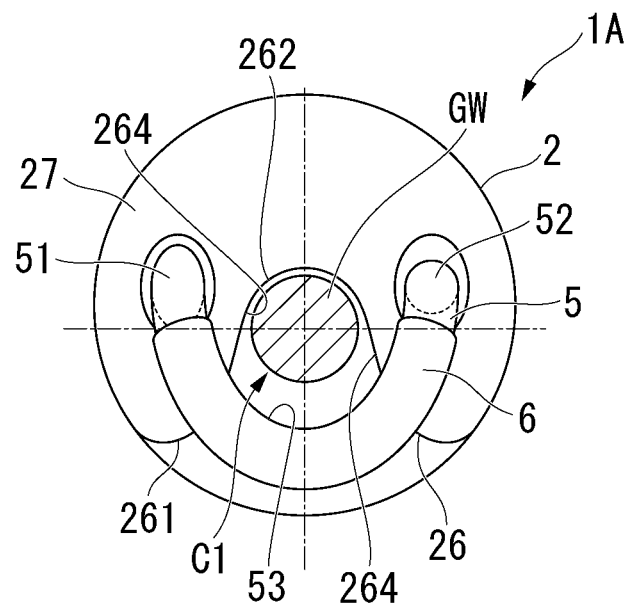
FIG. 13 is a front view of a guide wire holder of a first modified example of the an exemplary embodiment when seen from the distal side.

FIG. 13 is a front view of a guide wire holder 1A according to a first modified example. As shown in FIG. 13, a resin cover member 6 may be provided on the hook 5. The frictional resistance between the guide wire GW and the hook 5 is capable of being reduced by providing the resin cover member 6 on a portion of the hook 5 which protrudes from the sheath 2. As a result, when the sheath 2 is pushed along the guide wire GW, the sheath 2 is capable of being pushed in easily. The cover member 6 is not an essential component. For example, in addition to the resin cover, the hook may be coated with a lubricant or PTFE coating. In addition, when the closed regions C1 and C2 are sufficiently wide with respect to the diameter of the guide wire GW, contact between the guide wire GW and the hook 5 is curbed, and thus the cover member 6 is unnecessary.

Second Modified Example of First Embodiment

Figure 14:
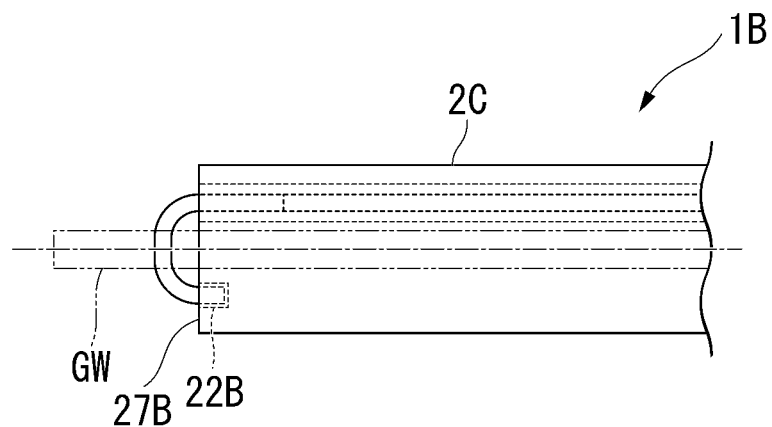
FIG. 14 is a top view showing a distal end portion of a guide wire holder of an exemplary embodiment when seen from the distal end side.

FIG. 14 is a top view of a guide wire holder 1B of a second modified example. The second modified example shown in FIG. 14 is different from the first embodiment in the constitution of the hook-accommodating lumen of the second end portion 52 of the sheath 2. In the second modified example, a bottomed concave portion 22B which opens to a distal end surface 27B of the sheath 2 is formed in the sheath 2. The concave portion 22B serves as the hook-accommodating lumen of the second end portion 52 when the hook 5 is located at the retracted position. In the first embodiment, an example in which the second lumen 22 in which a duct is formed over the entire length of the sheath 2 and through which a contrast medium or another wire is capable of being inserted is used as the hook-accommodating lumen is provided. However, for the purpose of accommodating the second end portion 52 of the hook 5, instead of the second lumen 22 formed over the entire length, a concave portion may be formed only at the distal end of the sheath 2 and the second end portion 52 may be accommodated in the concave portion. Since the hook-accommodating lumen is provided separately from the second lumen 22, the second lumen 22 is capable of being used for other purposes in a state in which the hook 5 is held at the retracted position. For example, the second guide wire is capable of being supplied from the second lumen 22 in the state in which the hook 5 is held at the retracted position.

Third Modified Example of First Embodiment

Figure 15:
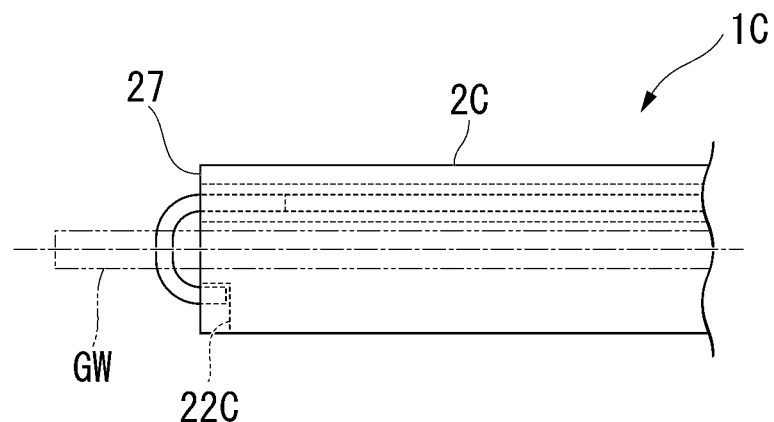
FIG. 15 is a top view showing a distal end portion of a guide wire holder of an exemplary embodiment when seen from the distal end side.
Figure 16:
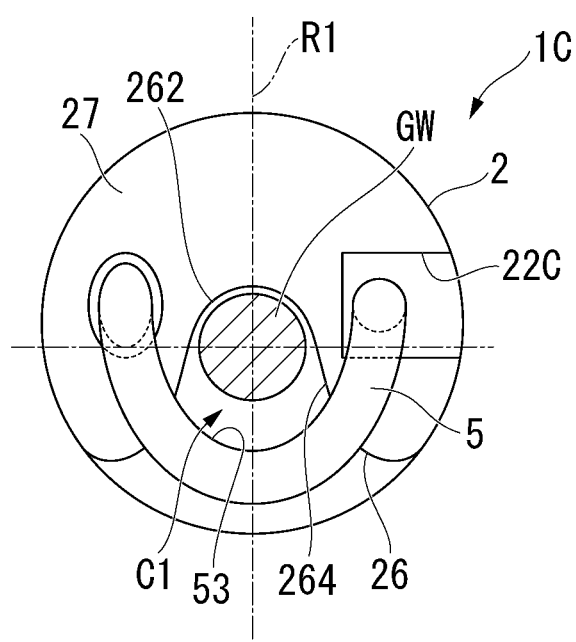
FIG. 16 is a front view of the guide wire holder shown in FIG. 15 when seen from the distal side.

FIG. 15 is a top view of a guide wire holder 1C of a third modified example. FIG. 16 is a front view of the guide wire holder 1C of the third modified example. The third modified example shown in FIGS. 15 and 16 is different from the concave portion 22B of the second modified example in a shape. A concave portion 22C of the third modified example is formed to be recessed in a region including a boundary portion between the distal end surface 27C of the sheath 2 and the outer peripheral surface thereof. Even when the hook-accommodating lumen which is capable of accommodating the second end portion 52 has such a constitution, the second end portion 52 is capable of being easily accommodated.

Fourth Modified Example of First Embodiment

Figure 17:
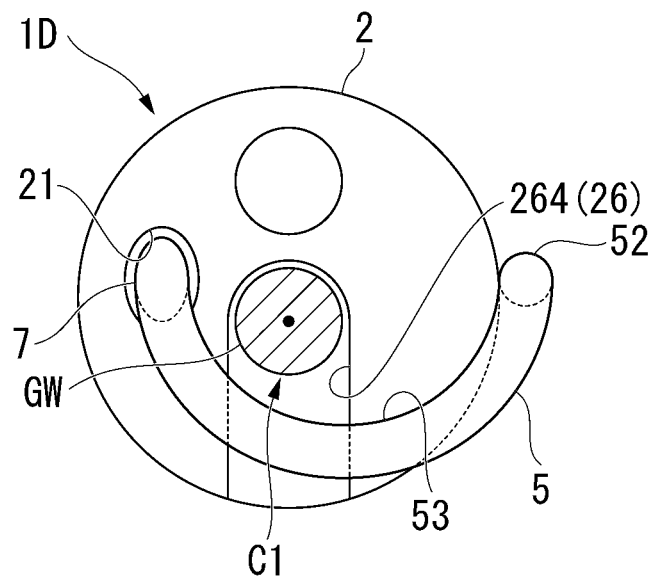
FIG. 17 is a front view of a guide wire holder of an exemplary embodiment when seen from the distal side.

FIG. 17 is a front view of a guide wire holder 1D of a fourth modified example. This modified example is an example without the hook-accommodating lumen. As shown in FIG. 17, when the hook 5 is disposed at the retracted position, the second end portion 52 may be located outward from the outer peripheral surface of the distal end of the sheath 2 to be disposed close thereto. Also in such a modified example, when the hook 5 is retracted to the retracted position, the second end portion 52 is capable of being located closer to the proximal side than the distal end of the sheath 2, and the closed region C1 is capable of being formed in a front view. When the hook-accommodating lumen is not provided and the hook 5 is disposed at the retracted position, the second end portion 52 may be in contact with or disposed close to the distal end of the sheath 2. When the second end portion 52 is disposed close to the distal end of the sheath 2 at the retracted position of the hook 5, and the separation distance LS between the second end portion 52 of the hook 5 and the distal end of the sheath 2 is smaller than the outer diameter of the guide wire, the guide wire GW is capable of being held.

Fifth Modified Example of First Embodiment

Figure 18:
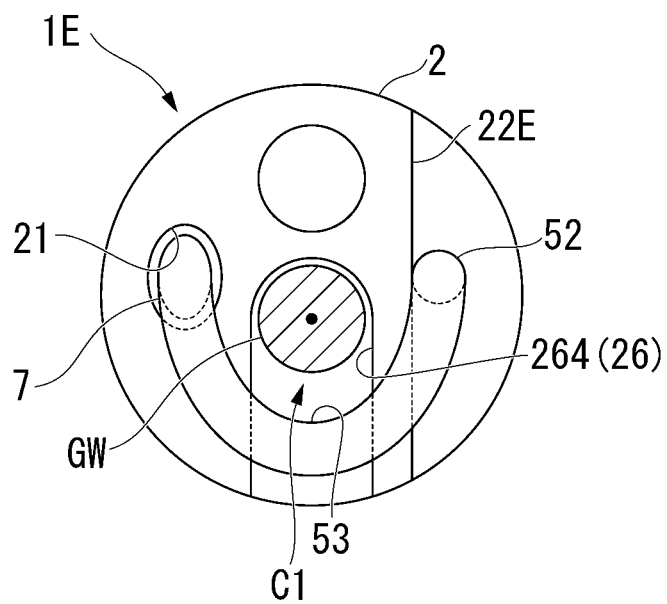
FIG. 18 is a front view of a guide wire holder of an exemplary embodiment when seen from the distal end side.

FIG. 18 is a front view of a guide wire holder 1E according to a fifth modified example. In this modified example, as shown in FIG. 18, an outer surface 22E which is substantially parallel to the longitudinal axis of the sheath 2 may be formed by D-cutting (cutting into a D-shape) a position of a distal end portion of a sheath 2E in which the second end portion 52 advances and retracts without forming the hook-accommodating lumen. Also in such a modified example, when the hook 5 is retracted to the retracted position, the second end portion 52 is capable of being located closer to the proximal side than the distal end of the sheath 2, and the closed region C1 is capable of being formed in a front view.

Sixth Modified Example of First Embodiment

Figure 19:
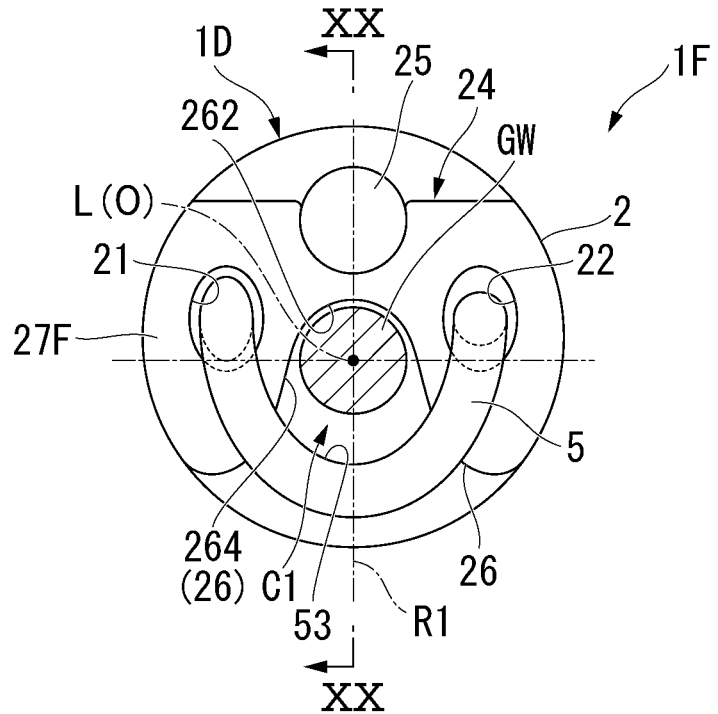
FIG. 19 is a front view of a guide wire holder of an exemplary embodiment when seen from the distal end.
Figure 20:
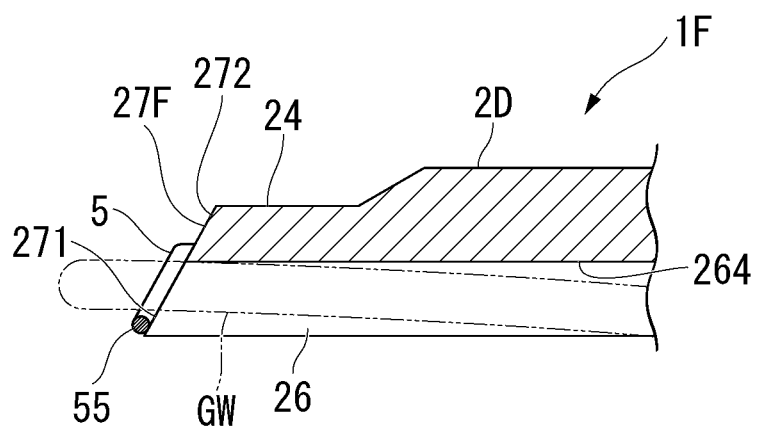
FIG. 20 is a cross-sectional view along line XX-XX in FIG. 19.

FIG. 19 is a front view of a guide wire holder 1F of a sixth modified example. FIG. 20 is a cross-sectional view along line XVII-XVII in FIG. 19. The sixth modified example shown in FIGS. 19 and 20 is different from the sheath 2 of the first embodiment in the shape and constitution of a distal end portion of a sheath 2F.

As shown in FIGS. 19 and 20, in this modified example, a cutout portion (a step) 24 is provided in a part of the distal end portion of the sheath 2F, and a dimension of the distal end portion of the sheath 2F is smaller than that of the proximal end side. The sheath 2F is capable of being more easily inserted into the duodenal papilla Dp by thus reducing a size of the distal end portion of the sheath 2F.

As shown in FIG. 19, in the sheath 2F of the modified example, the groove 26 and a contrast lumen 25 are arranged and provided in the direction of the first diameter line R1, and the cutout portion 24 is provided at a distal end portion of the contrast lumen 25. Therefore, a dimension of the cutout portion 24 in the direction of the longitudinal axis L is set to be equal to or less than a length in which the sheath 2F is inserted into the bile duct. This is because when the cutout portion 24 is longer than the length in which the sheath 2DF is inserted into the bile duct, a distal end opening of the contrast lumen is not inserted into the bile duct and the contrast medium cannot be injected into the bile duct. Further, preferably, the cutout portion 24 in the direction of the first diameter line R1 is formed to be cut out such that the first lumen 21 and the second lumen 22 do not communicate with the outside of the sheath 2F.

Further, in the above-described first embodiment, although the distal end surface 27 of the sheath 2 is formed by a surface of the sheath 2 orthogonal to the longitudinal axis L, a distal end surface 27F of the sheath 2F may be formed to be inclined with respect to the central axis O, as shown in FIG. 20. Specifically, in the distal end surface 27F of the sheath 2F may be formed to be inclined such that a portion 271 on the groove 26 side may be located on the distal end side and a portion 272 on the cutout portion 24 side may be located on the proximal side, and an inclination angle of the distal end surface 27F of the sheath 2F may be substantially parallel to an inclination angle of the hook 5 in a radial direction. In this way, in the case in which the part of the groove 26 side of the sheath 2F is located on the distal end side of the sheath, and the distal end surface 27F of the sheath 2F is inclined to be substantially parallel to the hook 5, the distal end of the sheath 2F is capable of being smoothly inserted along the guide wire GW held at the hook 5 and the distal end of the sheath 2F when a sheath 2D is inserted into the duodenal papilla Dp.

The mode in which the dimension of the distal end portion of the sheath 2F is made smaller than that of the proximal end side is not limited to the form shown in this modified example. For example, the distal end portion of the sheath may be tapered so that the distal end side becomes thinner over the entire circumference.

Seventh Modified Example of First Embodiment

Figure 21:
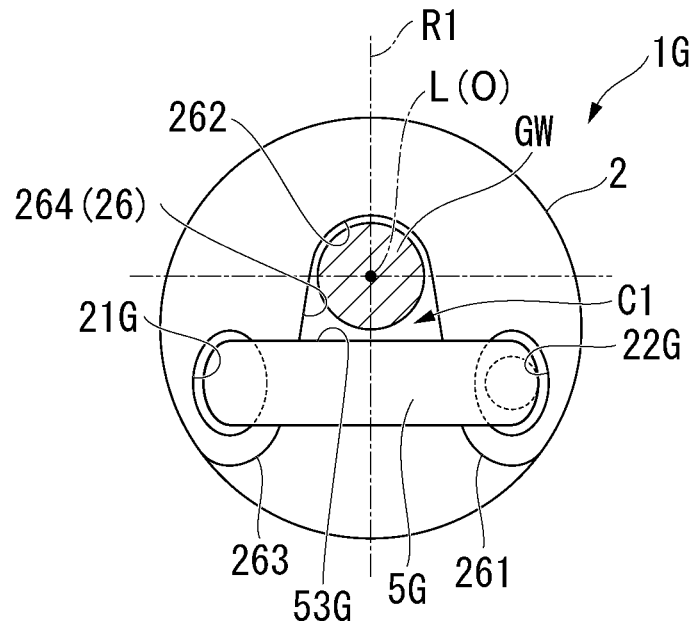
FIG. 21 is a front view of a guide wire holder of an exemplary embodiment when seen from the distal side.

FIG. 21 is a front view of a guide wire holder 1G of a seventh modified example. The seventh modified example is different from the first embodiment in the constitution of the hook 5G and a sheath 2G. In this modified example, a first lumen 21E and a second lumen 22G are formed closer to the outer peripheral opening portion 263 of the groove 26 than the bottom portion 262 of the groove 26. Further, the hook 5G is not curved in the radial direction and extends in the direction of the longitudinal axis L of the sheath 2G (a bending angle θ=180 degrees). Also with such a constitution, the closed region C1 is capable of being formed between the distal end edge 261 of the groove 26 and a guide wire engagement surface 53G of the hook 5G. Therefore, similarly to the above-described first embodiment, the guide wire GW is capable of being held in the closed region C1 while being accommodated in the groove 26, and the sheath 2G is capable of being easily advanced and retracted along the guide wire GW. The bending angle of the hook (refer to FIG. 5) is preferably a right angle or an obtuse angle (90 degrees or more and less than 180 degrees), and as the bending angle θ in this range becomes smaller, a large area of the closed region C1 is capable of being secured in a front view of the distal end of the sheath 2.

Eighth Modified Example of First Embodiment

Figure 22:
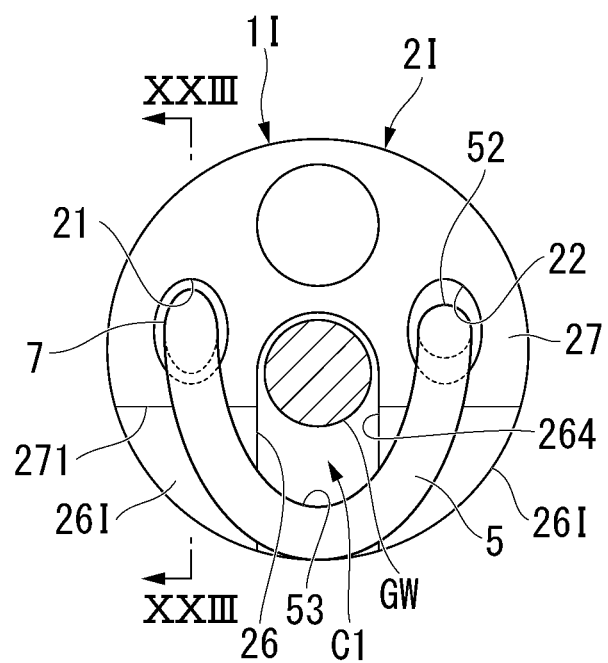
FIG. 22 is a front view of a guide wire holder of an exemplary embodiment when seen from the distal side.
Figure 23:
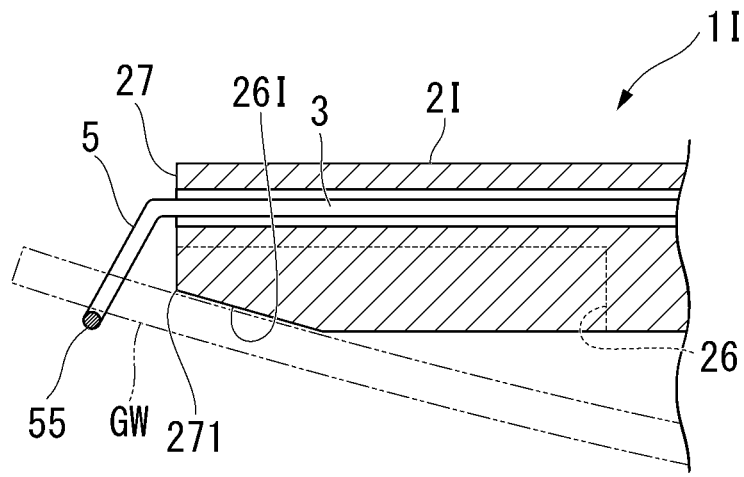
FIG. 23 is a cross-sectional view along line XXIII-XXIII in FIG. 22.

FIG. 22 is a front view of a guide wire holder 1I of an eighth modified example. FIG. 23 is a side view of FIG. 22.

In this modified example, in a front view, inclined surfaces (backcut surfaces) 26I may be provided on both sides of the groove 26 at a distal end portion of a sheath 2I. The inclined surface 26I is inclined from the distal end of the sheath 2I toward the proximal end side. In this case, when the hook 5 is pulled while the guide wire GW is hooked by the hook 5, the guide wire GW easily enters the groove 26.

Ninth Modified Example of First Embodiment

Figure 24:
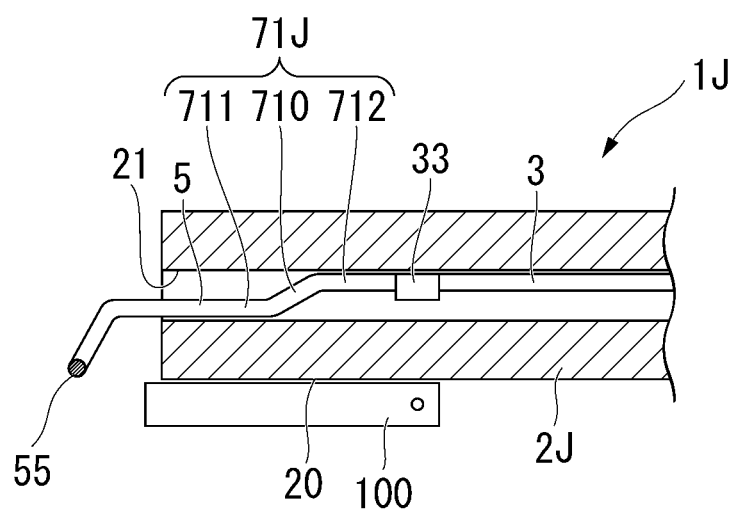
FIG. 24 is a cross-sectional view of a guide wire holder of an exemplary embodiment in a direction of a longitudinal axis.
Figure 25:
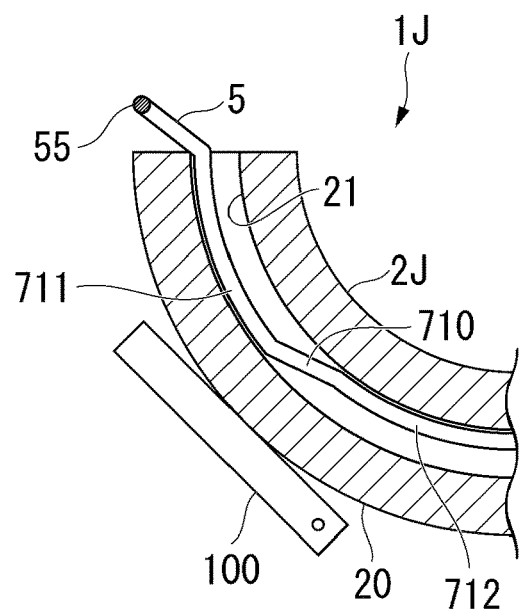
FIG. 25 is a cross-section view of the guide wire holder of an exemplary embodiment in the direction of the longitudinal axis.

FIGS. 24 and 25 are side views of a guide wire holder 1J according to a ninth modified example. The modified example is an example in which a constitution of the restricted portion is different from that of the above-described embodiment. The hook 5 extends to the distal end of the operation wire 3, and the hook 5 and the operation wire 3 are joined by a joint 33. A restricted portion 71J forms a bent portion 710 by bending an intermediate portion of a proximal end region of the hook 5. The restricted portion 71J has a first portion 711 which extends further to the distal side than the restricted portion 71J and a second portion 712 which extends toward the proximal side. That is, a bent portion between the joint 33 and the hook 5 constitutes the restricted portion 71. In this modified example, the restricted portion 71J is capable of being easily formed only by bending the hook 5.

The first portion 711 is located further outward with respect to the curve of the pre-curved portion 20 than the second portion 712, and the second portion 712 is located further inward with respect to the curve of the pre-curved portion. Further, the first portion 711 and the second portion 712 minimize a clearance to the inner wall of the first lumen 21. Therefore, as shown in FIG. 25, when a sheath 2J is raised by the forceps-elevator 100 provided in the endoscope insertion portion 201, even if a force from the forceps-elevator 100 is applied to the sheath 2J from the outside of the curve of the pre-curved portion 20, the first portion 711 which passes through the inside of the first lumen 21 is unlikely to be displaced inside the curve of the pre-curved portion 20. As a result, a relative position between the second end portion 52 of the hook 5 and the sheath 2J is capable of being prevented from being displaced. Therefore, even when the pre-curved portion 20 is curved by the forceps-elevator 100, a positional relationship between the second lumen 22 and the second end portion 52 is capable of being maintained.

Figure 26:
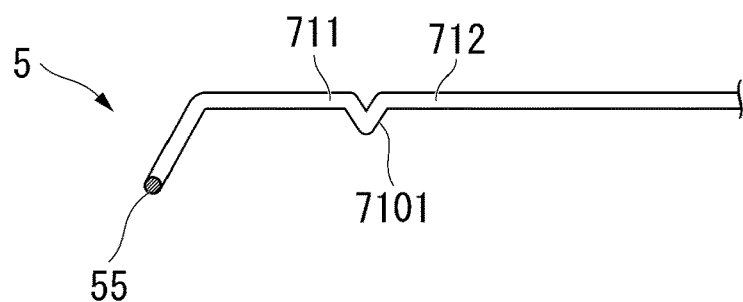
FIG. 26 is a side view showing a modified example of a restricted portion according to an exemplary embodiment.

The shape of the bent portion 710 of the restricted portion 71J is not limited to the shapes shown in FIGS. 24 and 25. For example, the modified example shown in FIG. 26 or 27 may be used. The modified example shown in FIG. 26 is an example in which, in a side view when the hook 5 is seen in a direction orthogonal to the longitudinal axis direction of the hook 5, a bent portion 7101 is bent into a V shape, and the first portion 711 and the second portion 712 are located substantially coaxially. The bent portion 7101 is disposed on the groove 26 side or the side surface side in the first lumen. In the case of this modified example, the first portion 711 and the second portion 712, and a vertex portion of the bent portion 7101 are in contact with the first lumen 21 to restrict the rotation of the hook 5 with respect to the sheath 2J.

Figure 27:
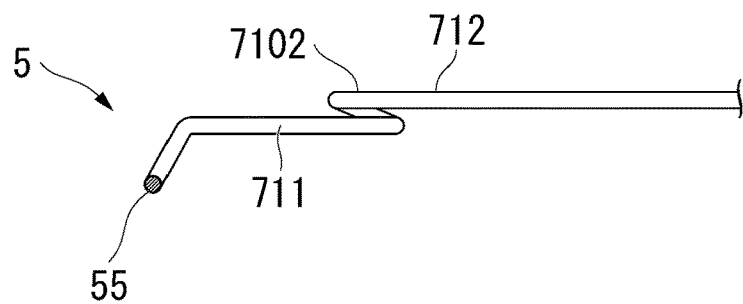
FIG. 27 is a side view showing the modified example of the restricted portion according to an exemplary embodiment.

In the modified example shown in FIG. 27, in a side view when the hook 5 is seen in the direction orthogonal to the longitudinal axis direction of the hook 5, a bent portion 7102 is bent into a Z shape, and the first portion 711 and the second portion 712 have their axes offset in the radial direction. In this modified example, when the sheath 2J is raised by the forceps-elevator 100 as in the restricted portion 71J shown in FIG. 24, even if a force from the forceps-elevator 100 is applied to the sheath 2J from the outside of the curve of the pre-curved portion 20, the first portion 711 which passes through the inside of the first lumen 21 is unlikely to be displaced inside the curve of the pre-curved portion 20.

Tenth Modified Example of First Embodiment

Figure 28:
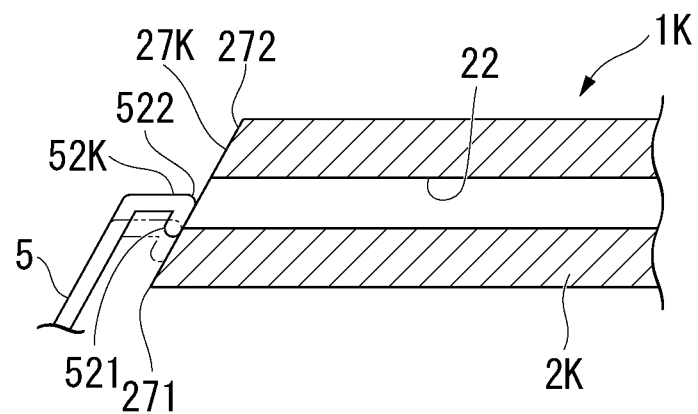
FIG. 28 is a cross-sectional view of a guide wire holder of an exemplary embodiment in a direction of a longitudinal axis.

FIG. 28 is a view schematically showing a cross section of a guide wire holder 1K of a tenth modified example in the longitudinal axis direction. In this modified example, as in the sheath 2F of the sixth modified example, a distal end surface 27K of a sheath 2K is formed to be inclined with respect to the central axis O. A portion 271 of the distal end surface 27K of the sheath 2K on the groove 26 side is inclined to be located on the distal end side of the sheath. Further, the shape of a second end portion 52K of the hook 5 is different from that in the above-described first embodiment. Specifically, a bent portion 522 is formed at a proximal end of the second end portion 52K in direction of the longitudinal axis. The bent portion 522 is folded back in a direction which intersects the longitudinal axis of the second lumen 22, and an end portion 521 extends at the same angle as the inclination angle of the distal end surface 27K. The end portion 521 of the second end portion 52K extends in a direction which intersects the longitudinal axis of the second lumen 22. In this case, when the hook 5 moves toward the proximal side, the end portion 521 comes into contact with the inclination of the distal end surface 27K of the sheath 2 and slides, and thus the second end portion 52K of the hook 5 is easily accommodated in the second lumen 22.

Eleventh Modified Example of First Embodiment

Figure 29:
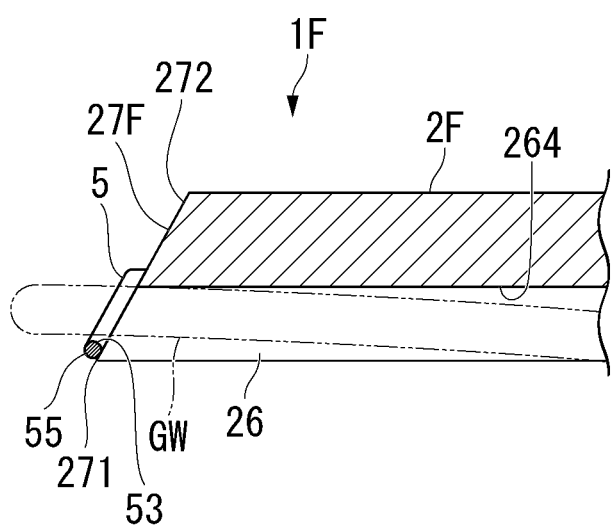
FIG. 29 is a cross-sectional view of a guide wire holder of an exemplary embodiment in the direction of the longitudinal axis.

As for the shape of the distal end of the sheath in each of the embodiments and the modified examples, the distal end surface 27F of the sheath 2F may be inclined to have a tapered shape as in an eleventh modified example shown in FIG. 29. Since the distal end surface 27F of the sheath 2F is inclined to have a tapered shape in this way, the sheath 2F is easily inserted into the duodenal papilla Dp.

Second Embodiment

A guide wire holder 1H according to a second embodiment will be described with reference to FIGS. 30 to 32. The guide wire holder 1H according to the second embodiment is different from the first embodiment in the constitution of the distal end portion. Therefore, only the distal end portion of the guide wire holder 1H is shown, and the description of the operation portion will be omitted. Further, in the following description, the same components as those already described will be designated by the same reference numerals, and redundant description thereof will be omitted.

Figure 30:
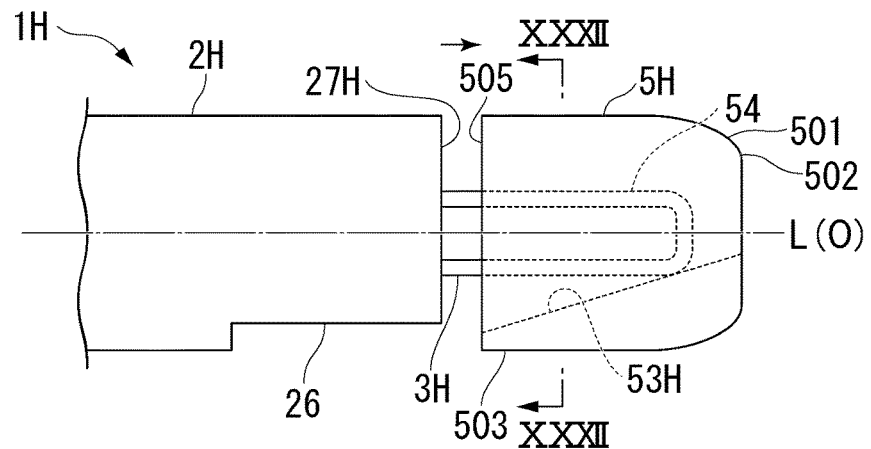
FIG. 30 is a side view showing a distal end portion of a guide wire holder according to an exemplary embodiment.

FIG. 30 is a side view showing the distal end portion of the guide wire holder 1H according to the embodiment. FIG. 31 is a cross-sectional view taken along the central axis O of FIG. 30. FIG. 32 is a cross-sectional view taken along line XXXII-XXXII in FIG. 30.

The guide wire holder 1H according to the embodiment is different from that of the first embodiment in the constitution of the hook. A hook 5H is a three-dimensional member fixed to a distal end portion of an operation wire 3H. The hook 5H has a substantially cylindrical outer shape, and a slit 56 is formed in the direction of the longitudinal axis L. As shown in FIGS. 30 and 31, an R surface 502 is formed on an outer peripheral portion of a distal end portion 501 of the hook 5H. As shown in FIG. 32, the slit 56 is a groove which opens on the first diameter line R1 on the outer peripheral surface of the hook 5H and is recessed in the radial direction. The slit 56 is formed to extend over the entire length of the hook 5H in the direction of the longitudinal axis L. In the example shown in FIG. 32, the slit 56 is a groove having a U shape, and a bottom surface of the slit 56 is a guide wire engagement surface 53H.

Figure 31:
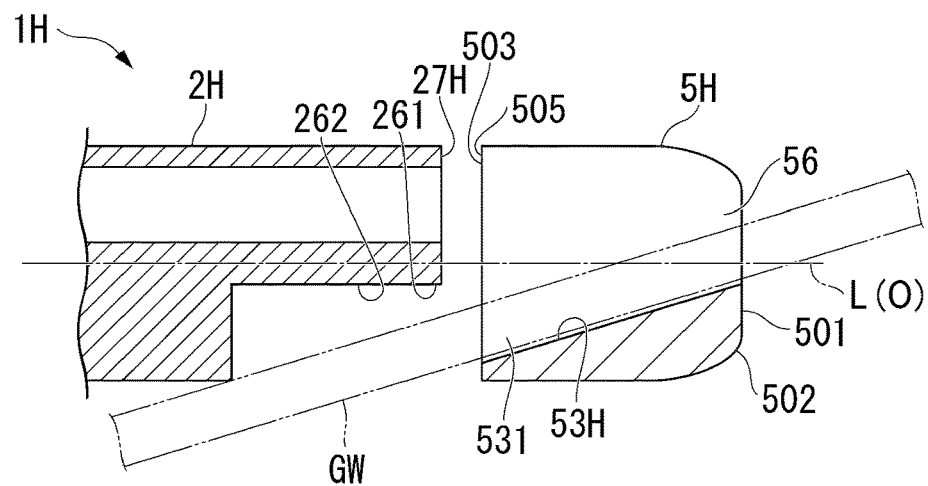
FIG. 31 is a cross-sectional view showing the distal end portion of the guide wire holder according to an exemplary embodiment in a direction of a longitudinal axis.
Figure 32:
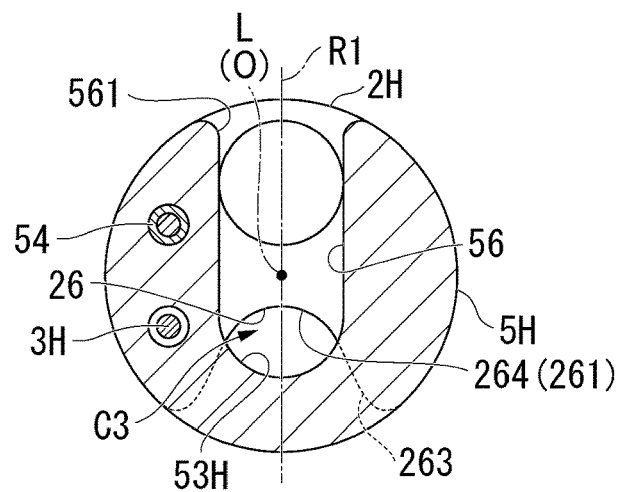
FIG. 32 is a cross-sectional view along line XXXII-XXXII in FIG. 34.

As shown in FIGS. 31 and 32, the slit 56 opens in a direction opposite to the opening of the groove 26 of the sheath 2H. That is, the outer peripheral opening portion 263 of the groove 26 and an opening 561 of the slit 56 open on the first diameter line R1 and are open in different directions by 180 degrees in the circumferential direction. Further, when seen in the direction of the longitudinal axis (in a front view along the longitudinal axis), the guide wire engagement surface 53H of the slit 56 preferably intersects the curved distal end edge (the ridge line) 261 of the groove 26 to form a closed region C3. On the other hand, as shown in FIG. 31, in the direction of the longitudinal axis L, the bottom portion 262 of the groove 26 and the guide wire engagement surface 53H do not face each other, and the slit 56 is located on the distal end side from the distal end edge of the groove 26.

As shown in FIG. 31, the guide wire engagement surface 53H is inclined to approach an extension line of the central axis O of the sheath 2H as it goes from the proximal end of the hook 5H toward the distal end. A position of the guide wire engagement surface 53H at a proximal end portion 503 of the hook 5H in the radial direction is located radially outward from a position of the bottom portion 262 of the groove 26 of the sheath 2H. The closed region C3 may be formed as a region which is closed by at least the proximal end portion of the hook 5H and the distal end edge 261 of the groove 26 of the sheath 2 when seen in the direction of the longitudinal axis. Therefore, the guide wire GW captured in the closed region C3 can smoothly advance and retract in the closed region C3. As a result, when the distal end portion of the guide wire holder 1H is inserted into the duodenum, the sheath 2H is capable of being easily advanced along the guide wire GW. The groove 26 of the sheath 2H is formed on the extension of the inclination of the guide wire engagement surface 53H.

The hook 5H is a member formed of a resin. The hook 5H may be formed of any material which has sufficient strength when it is formed into a small shape in consideration of papilla insertability. When the hook 5H is formed of a resin, for example, ABS, PEEK, PSU, PPSU or the like is capable of being used. The hook may be formed of a metal. Further, the hook may be formed by combining a metal and a resin. For example, when an inner wall surface of the slit is formed of a resin, the guide wire GW is capable of being slid smoothly.

As shown in FIGS. 30 and 32, the hook 5H has a wire-fixing portion 54 into which the operation wire 3H is inserted and fixed. The wire-fixing portion 54 is provided between the slit 56 and the outer peripheral surface of the hook 5H. The wire-fixing portion 54 has a U-shaped communication hole in which two lumens extending parallel to the direction of the longitudinal axis L communicate with each other at the distal end portion, and the operation wire 3H is inserted into the communication hole and then fixed by, for example, an adhesive. A method for fixing the operation wire 3H and the wire-fixing portion 54 is not limited to the adhesive and may be performed by fitting, crimping, or the like.

As for the operation wire 3H, as shown in FIG. 30, two operation wires 3H extend in the direction of the longitudinal axis L. The two operation wires 3H are folded back within the distal end portion of the hook 5H and extend parallel toward the proximal side. The constitution in which the two operation wires 3H are folded back within the distal end portion of the hook 5H is not essential. The operation wires 3H are inserted in a first lumen (not shown) of the sheath 2H to be able to advance and retract. In the embodiment, both of the two operation wires 3H are inserted in the first lumen to be able to advance and retract, and the second lumen of the first embodiment is not included. When the operation wires 3H are advanced and retracted respect to the sheath 2H, the hook 5H can advance and retract with respect to the sheath 2H.

The guide wire engagement surface 53H of the hook 5H and the inner wall surface 264 of the groove 26 of the sheath 2H are disposed so that the guide wire GW is capable of being held between the hook 5H and the groove 26 to be able to advance and retract. Since the guide wire engagement surface 53H of the slit 56 is inclined so that the distal end portion of the slit 56 is located near the central axis O of the sheath 2H, the guide wire GW is held at the distal end portion 501 of the hook 5H to be located near the central axis O of the sheath 2. As a result, when the distal end portion of the guide wire holder 1H is inserted into the duodenum, the sheath 2H is capable of being easily advanced along the guide wire GW.

According to the guide wire holder 1H of the embodiment, the guide wire GW is capable of being easily hooked by the hook 5H by disposing the hook 5H at the advanced position. Also, when the guide wire GW is hooked by the hook 5H, since the opening 561 of the slit 56 is capable of being visually recognized under the endoscopic image, the guide wire GW is capable of being easily guided into the slit 56 of the hook 5H, and the guide wire GW is capable of being easily hooked in the slit 56. Also, in a state in which the guide wire GW is hooked on the guide wire engagement surface 53H, the guide wire GW is capable of being inserted into the groove 26 of the sheath 2H by retracting the hook 5H (disposing the hook 5H in the retracted position). At this time, preferably, a proximal end surface 505 of the proximal end portion 503 of the hook 5H comes into contact with a distal end surface 27H of the sheath 2, and thus the hook 5H, particularly the guide wire engagement surface 53H is positioned distant from the distal end of the groove 26. In this state, the guide wire GW is held between the guide wire engagement surface 53H and the inner wall surface 264 of the groove 26. According to the guide wire holder 1H according to the embodiment, as in the first embodiment, the sheath 2H is capable of being smoothly inserted into the papilla side along the guide wire GW.

Since the guide wire holder 1H according to the embodiment is constituted to fix the three-dimensional hook 5H having the slit 56 to the distal end portion of the operation wire 3H, the guide wire GW is capable of being easily captured in the slit 56, and also, when the hook 5H is disposed at the retracted position, the guide wire GW is capable of being easily held in the closed region C3 between the guide wire engagement surface 53H and the inner wall surface 264 of the groove 26. Further, the guide wire GW is capable of being prevented from coming off from the hook 5H by disposing the hook 5H at the retracted position. As a result, for example, the sheath 2H is capable of being smoothly inserted into the papilla side.

Since the guide wire holder 1H according to the embodiment has a constitution in which the three-dimensional hook 5H is fixed to the operation wire 3H, the diameter of the operation wire is capable of being reduced when compared to the case in which the linear hook 5 like the operation wire 3 of the first embodiment is used. Therefore, a highly flexible operation wire is capable of being used, and flexibility of the operation wire 3H inserted into the sheath 2H is improved. As a result, the flexibility of the entire guide wire holder 1H is significantly improved, and the flexibility of the entire device is capable of being increased. When the flexibility of the entire device is high, operability as a device for cannulation is improved.

The guide wire holder according to the present invention is not limited to the example of the above-described second embodiment. For example, the modified examples shown in FIGS. 33 to 42 is capable of being provided. In the following description, the same components as those already described will be designated by the same reference numerals, and duplicate description thereof will be omitted.

First Modified Example of Second Embodiment

Figure 33:
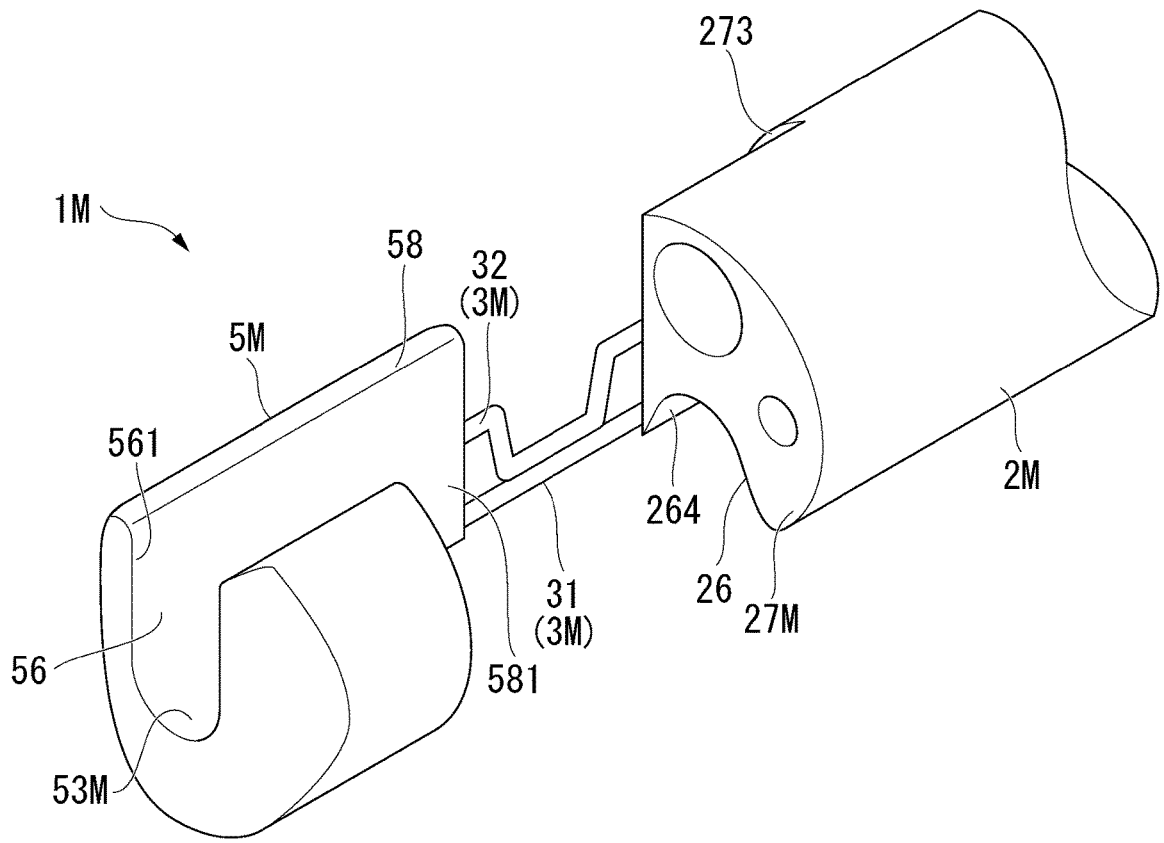
FIG. 33 is a perspective view of a guide wire holder of an exemplary embodiment.
Figure 34:
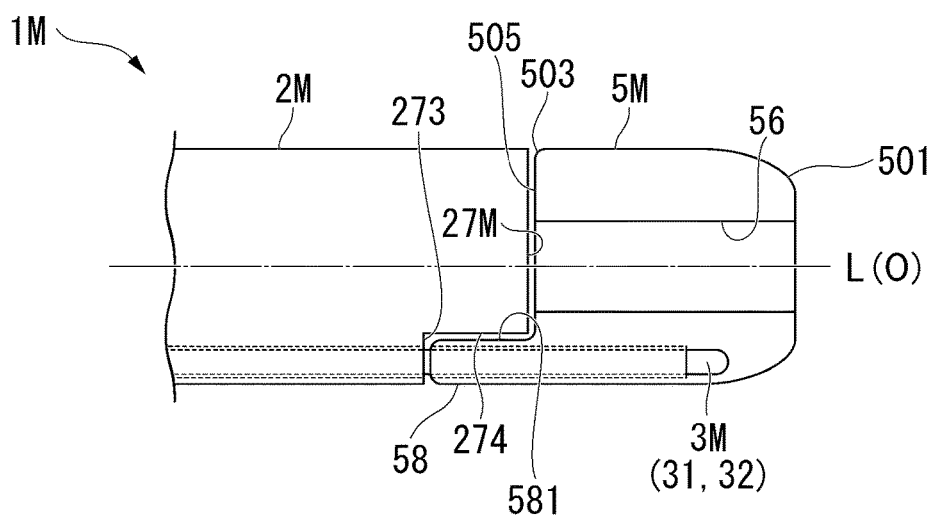
FIG. 34 is a top view of the guide wire holder of an exemplary embodiment.
Figure 35:
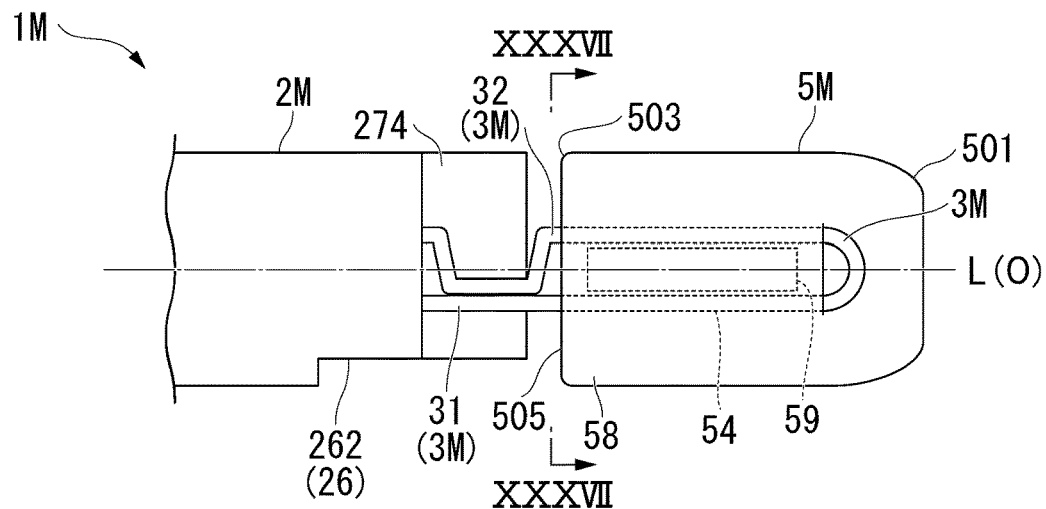
FIG. 35 is a top view of the guide wire holder of an exemplary embodiment.

FIG. 33 is a perspective view of a distal end portion of a guide wire holder 1M according to a first modified example of the second embodiment. FIG. 34 is a top view of the distal end portion of the guide wire holder 1M of the modified example, and FIG. 35 is a side view of the distal end portion of the guide wire holder 1M of the modified example. This modified example is different from the second embodiment in the constitution of a hook 5M, a sheath 2M, and an operation wire 3M.

In the second embodiment, the example in which the proximal end portion 503 of the hook 5H is formed in a planar shape is shown. However, in the hook 5M of the modified example, a protrusion 58 which protrudes further toward the proximal side than the proximal end surface of the hook 5M is provided. The protrusion 58 is formed in a region in which the wire-fixing portion 54 is provided, and the protrusion 58 protrudes toward the sheath 2 side along the operation wire 3M. The protrusion 58 includes a contact surface 581 which can come into contact with a side surface of the sheath 2M when the hook 5M is retracted.

A distal end portion of the sheath 2M includes the groove 26 similarly to the sheath 2H of the second embodiment. A step portion 273 in which a region of a first lumen 21M in which the operation wire 3M is inserted is recessed toward the proximal side is formed on a distal end surface 27M of the sheath 2M. The step portion 273 has a side surface 274 formed by cutting out in a plane shape along the longitudinal axis L. The protrusion 58 may be set so that at least one of a proximal end of the protrusion 58 of the hook 5M or a proximal end surface 503 is in contact with the sheath 2 when the hook 5M is disposed at the retracted position. For example, the protrusion 58 may be set so that the hook 5M, particularly, the guide wire engagement surface 53M is positioned distant from the distal end of the groove 26 when the proximal end of the protrusion 58 is in contact with the step portion 273. In a state in which the proximal end of the protrusion 58 is in contact with the step portion 273, preferably, a slight gap is formed between the proximal end surface 505 (excluding the protrusion 58) of the hook 5M and the distal end surface 27M of the sheath 2M. Further, for example, the protrusion 58 may be set so that the proximal end surface 505 (excluding the protrusion 58) of the hook 5M and the distal end surface 27M of the sheath 2M come into contact with each other. In this case, preferably, a slight gap is formed between the proximal end of the protrusion 58 and the step portion 273. In the state in which the hook 5M and the sheath are in contact with each other as described above, the guide wire GW is held between the guide wire engagement surface 53M and the inner wall surface 264 of the groove 26.

Figure 36:
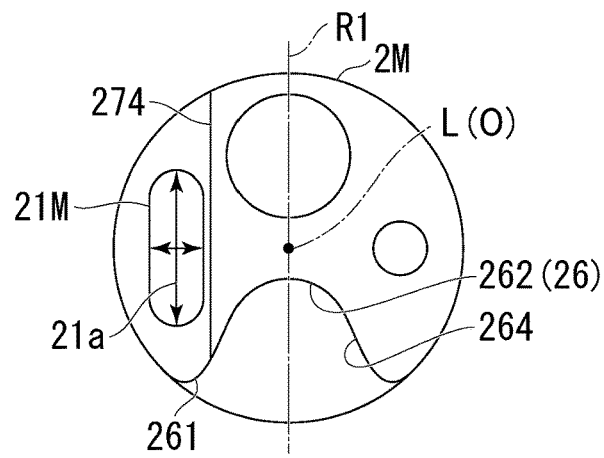
FIG. 36 is a front view of a sheath of t an exemplary embodiment.
Figure 37:
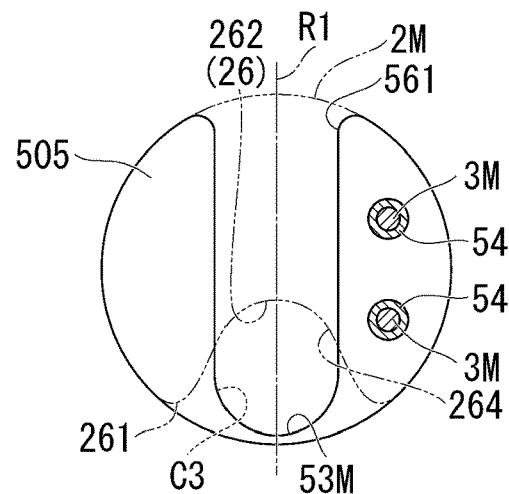
FIG. 37 is a cross-sectional view along line XXXVII-XXXVII in FIG. 35.

The operation wire 3M is provided by two operation wires 31 and 32 extending in the direction of the longitudinal axis L. A first operation wire 31 of the two operation wires 31 and 32 extends linearly to be parallel to the longitudinal axis L, and a second operation wire 32 is provided to be bent at a plurality of places to be uneven in the vertical direction in a side view. A proximal end of the first operation wire 31 is fixed to the operation slider 42 of the operation portion 4. A proximal end of the second operation wire 32 is disposed in the first lumen 21M. That is, the proximal end of the second operation wire 32 is disposed in the first lumen 21M without being connected to the operation portion 4. As shown in FIG. 34, the first operation wire 31 and the second operation wire 32 extend to overlap the longitudinal axis L in a top view. The first operation wire 31 and the second operation wire 32 are inserted through the first lumen 21M of the sheath 2M to be able to advance and retract. As shown in FIG. 36, the first lumen 21M has a long elliptical shape at least in the distal end opening portion thereof. The first lumen 21M is formed so that a long side 21a of the first lumen 21M is parallel to the side surface 274. With such a constitution, the first lumen 21M and the side surface 274 serve as a restricting portion, and the two operation wires 31 and 32 and the contact surface 581 serve as a restricted portion. As a result, the rotation around the axis is restricted more stably than a constitution in which the operation wire is restricted only by the first lumen 21M.

As a result of having a constitution in which the first operation wire 31 is connected to the operation portion 4 and the proximal end of the second operation wire 32 having the unevenness in the vertical direction is not connected to the operation portion 4, the uneven shape in the vertical direction of the second operation wire 32 is stably held, and the rotation of the hook 5H around the axis is capable of being effectively prevented. That is, when a force is applied to the hook 5H in a direction in which the hook 5H is pulled toward the proximal side, for example, when the operation slider 42 is pulled, it is difficult for an external force to be applied to the second operation wire 32, and deformation of the uneven shape in the vertical direction is prevented. Therefore, when the operation wire has the uneven shape which serves as the restricted portion, the uneven shape is preferably provided on the operation wire of which the proximal end of the operation wire is not connected to the operation portion 4 among the two operation wires.

Figure 38:
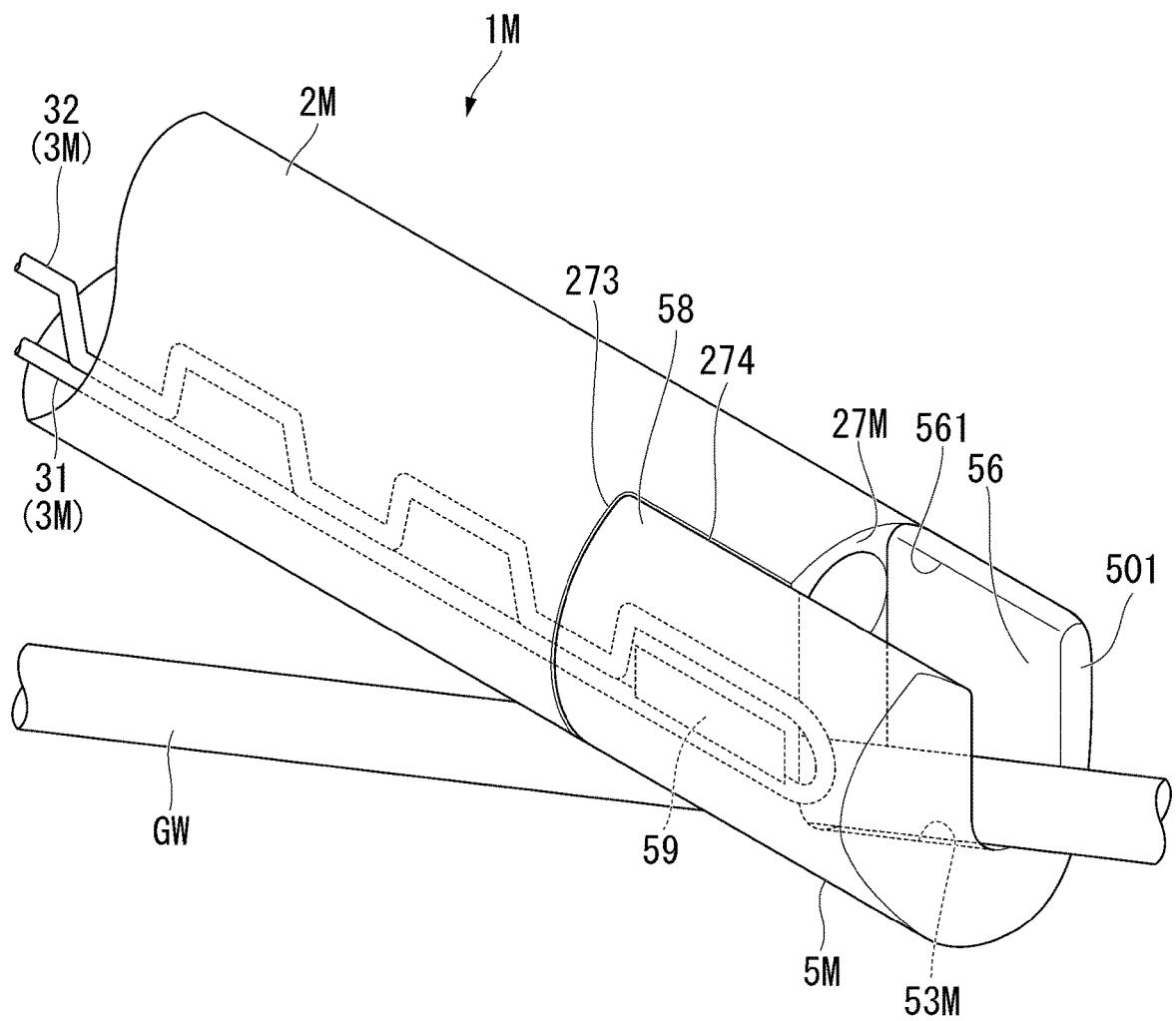
FIG. 38 is a schematic view showing an aspect when the guide wire holder according to an exemplary embodiment is used.
Figure 39:
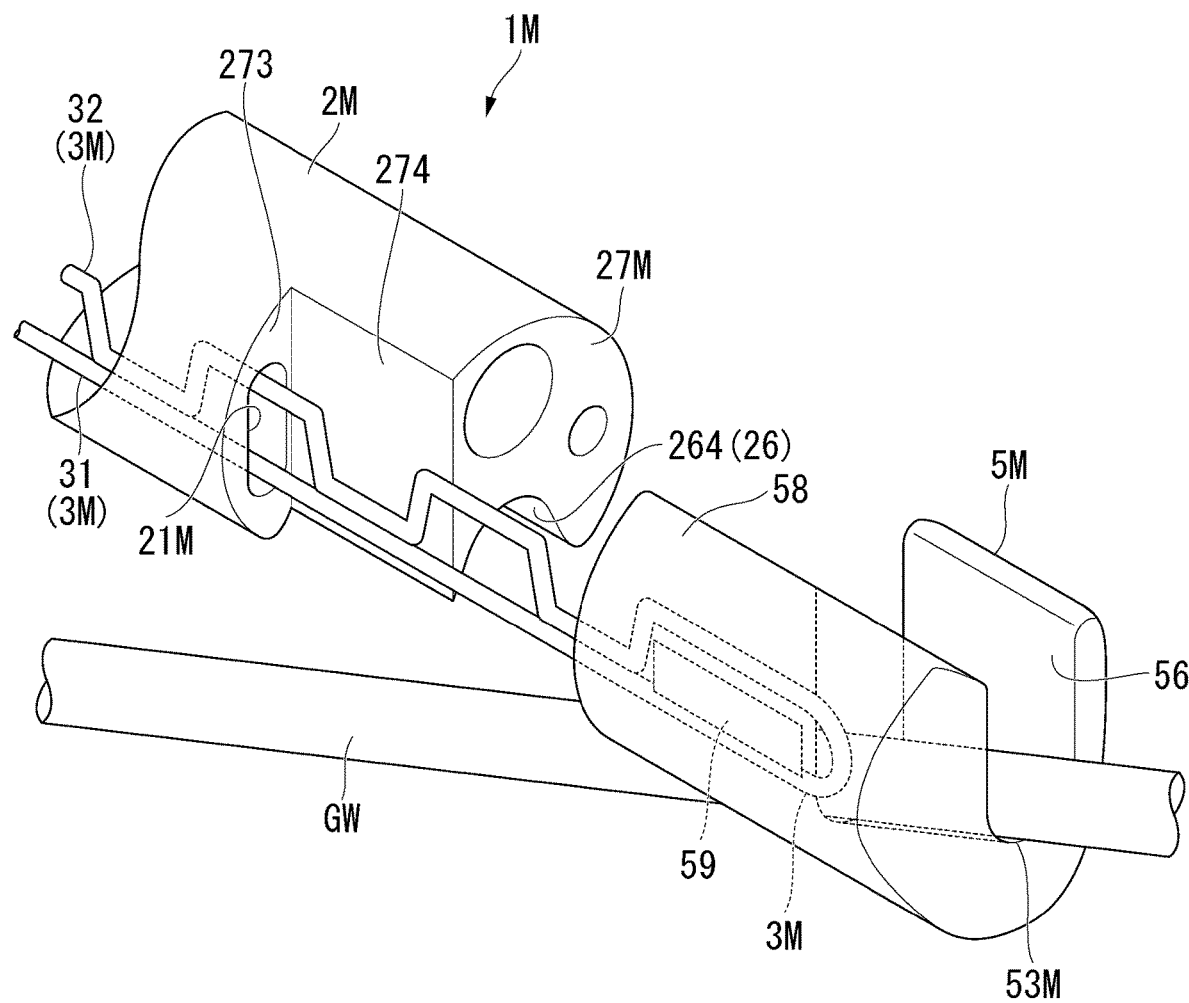
FIG. 39 is a schematic view showing the aspect when the guide wire holder according to an exemplary embodiment is used.
Figure 40:
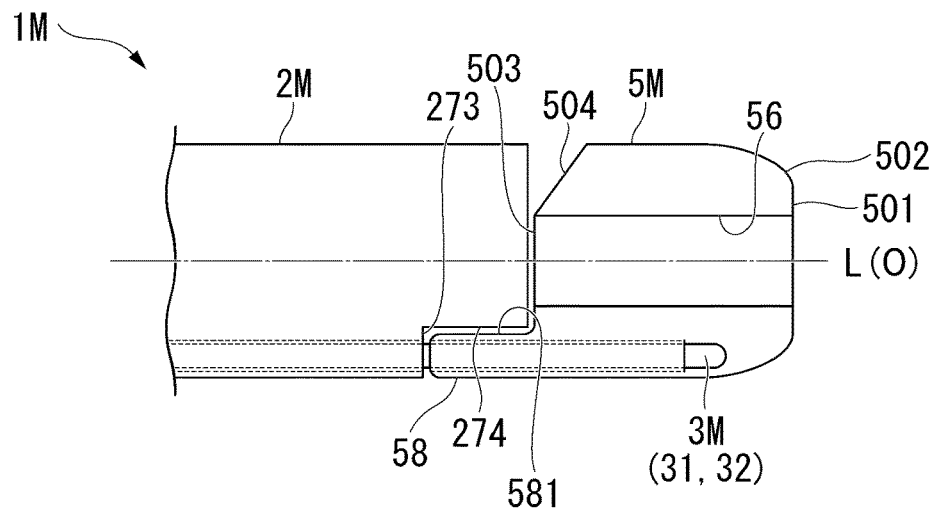
FIG. 40 is a top view of a guide wire holder of an exemplary embodiment.
Figure 41:
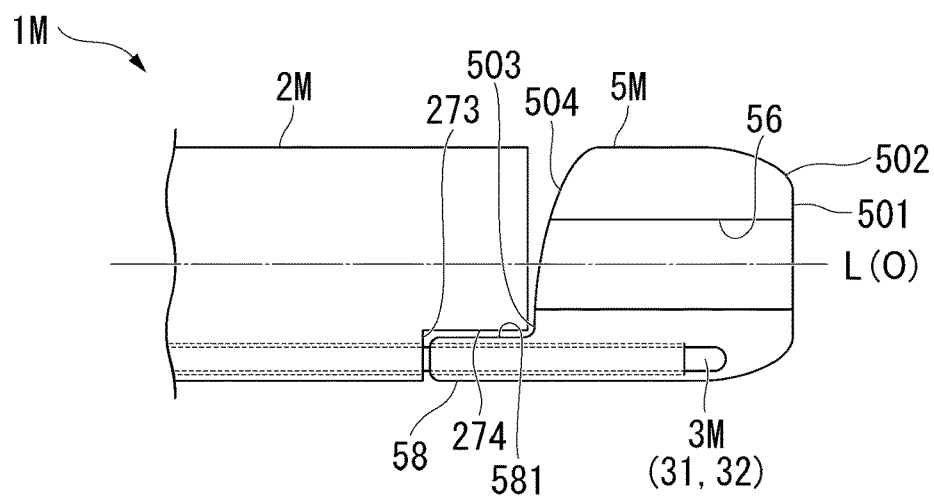
FIG. 41 is a top view of a guide wire holder of an exemplary embodiment.
Figure 42:
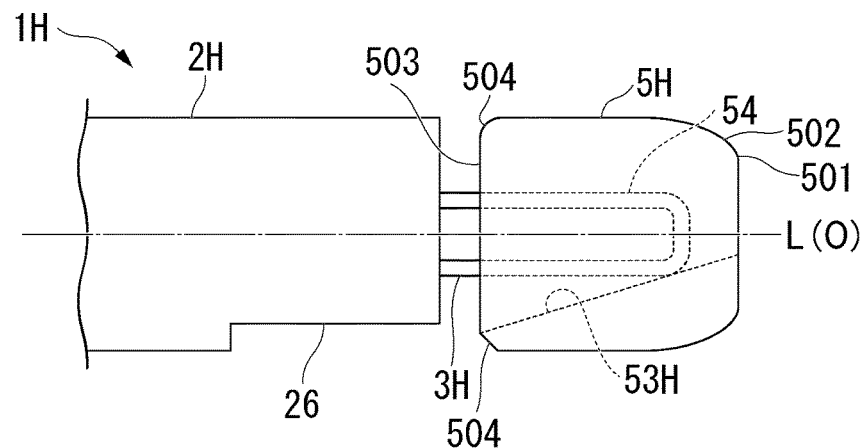
FIG. 42 is a top view of a guide wire holder of an exemplary embodiment.

As shown in FIGS. 35, 38, and 39, an X-ray marker 59 which is capable of being visually recognized in an X-ray image is provided at the hook 5M. In the modified example, the X-ray marker 59 is disposed in a folded-back portion of the distal end portion of the operation wire 3M and is embedded in the hook 5M.

In the embodiment, the contact surface 581 is formed continuously from the inner wall surface of the slit 56, but the contact surface 581 may be provided separately from the slit 56. The protrusion 58 may be provided at a position different from that of the wire-fixing portion 54.

For example, the constitution of the restricted portion in each of the embodiments and the modified examples is not limited to the above-described aspect. For example, the restricted portion in the second embodiment or the first modified example of the second embodiment may be changed to the restricted portion having the shape shown in FIGS. 24 to 27.

In the embodiment and the first modified example, since the R surface 502 is formed on the outer peripheral portion of the distal end portion 501 of each of the hooks 5M and 5H, the guide wire holders 1H and 1M is capable of being smoothly advanced and retracted. In addition, the R surface may be also formed on the proximal end portions 503 of the hooks 5M and 5H. Further, as long as the guide wire holder is capable of being smoothly advanced and retracted, shapes of the outer peripheral portions of the distal end portion and the proximal end portion of the hook are not limited to the R surface. For example, it may be a C surface. Further, as in the second modified example shown in FIG. 40, the distal end portion 501 of the hook may have the R surface 502, and the proximal end portion 503 may have the inclined surface 504 which is the C surface. In addition, as in the third modified example shown in FIG. 41, at the proximal end portion 503 of the hook 5M, the inclined surface 504 which is, for example, the R surface or the C surface may be formed so that a cutout amount increases as it is separated from a portion, to which the operation wire 3M is connected, in the radial direction of the hook 5M. Since such an inclined surface is formed at the proximal end portion of the hook 5M, it is difficult for the hook 5M to be caught in the tissue when the hook 5M is pulled toward the proximal side. Regarding the hook 5H of the second embodiment, although an example in which the proximal end surface is flat and the outer peripheral edge portion does not have the inclined surface is shown, as in the fourth modified example shown in FIG. 42, the inclined surface 504 may also be formed by, for example, the C surface or the R surface in the proximal end portion 503 of the hook 5H of the second embodiment. In the guide wire holder, the inclined surfaces of the proximal end portion and the distal end portion are not essential constitutions.

The protrusion 58 shown in the first modified example 5M of the second embodiment is not an essential constitution.

The X-ray marker is not limited to the aspect shown in the modified example of the second embodiment, and at least a part of the hook may be formed of a radiopaque material. For example, the X-ray marker may be provided on the operation wire or may be provided to be exposed on the outer peripheral surface of the hook 5H. Alternatively, when the hook itself is formed of a material having radiopacity, the X-ray marker is not essential.

The X-ray marker may be provided on the hook of the first embodiment or the second embodiment, or at least a part of the hook may be formed of a material having radiopacity.

The constitution of the operation wire 3H of the second embodiment and the constitution of the operation wire 3M of the modified example may be exchanged.

Although one embodiment of the present invention has been described above, the technical scope of the present invention is not limited to the above-described embodiment, and it is possible to add various changes to each of the components, to delete each of the components, or to combine the components of each of a without departing from the spirit of the present invention.

What is claimed is:

1. A guide wire holder, comprising:
a sheath including a lumen and a central axis that extends longitudinally;
an operation wire that is inserted through the lumen, the operation wire configured to advance and retract along a longitudinal axis that is parallel to the central axis; and
a hook that is continuous with a distal end of the operation wire and protrudes from a distal end of the sheath, wherein:
the sheath has an inner wall surface that includes a groove configured to extend from the distal end of the sheath to a proximal end side of the sheath and the groove having a concave shape that is recessed in a direction orthogonal to the central axis,
the groove has an opening portion that opens to an outer peripheral surface of the sheath,
the hook has a guide wire engagement surface configured to engage with a guide wire, and
the guide wire engagement surface and the inner wall surface are configured to hold the guide wire therebetween,
the hook includes a slit, the slit having a bottom surface that defines the guide wire engagement surface, and
the groove of the sheath and the slit open in opposite directions.

2. The guide wire holder according to claim 1, wherein:
a pre-curved portion having a curved shape is provided at a distal end portion of the sheath.

3. The guide wire holder according to claim 1, wherein the hook and the inner wall surface support the guide wire so that the guide wire is configured to advance and retract along the sheath, the guide wire configured to remain between the hook and the inner wall surface.

4. The guide wire holder according to claim 1, wherein the inner wall surface that defines the groove is a curved surface.

5. The guide wire holder according to claim 1, wherein the guide wire engagement surface at a proximal end portion of the hook intersects a ridge line of the inner wall surface in a front view in a direction along the longitudinal axis, and a closed region closed by the inner wall surface and the guide wire engagement surface is formed.

6. The guide wire holder according to claim 1, wherein the guide wire engagement surface is inclined toward an extension line of the central axis of the sheath from a proximal end of the hook toward a distal end of the hook.

7. The guide wire holder according to claim 1, wherein a protrusion which protrudes further proximal side than a proximal end surface of the hook and configured to be capable of being coming into contact with a side surface of the sheath when the hook is retracted is formed.

8. The guide wire holder according to claim 1, comprising a rotation-preventing portion including:
a restricting portion provided in the lumen in a direction of the longitudinal axis, an opening shape of the lumen in a cross section orthogonal to the longitudinal axis being an imperfect circle; and
a restricted portion provided in the operation wire in an axis direction, has an imperfect circle cross-sectional shape orthogonal to the axis, and is configured to be capable of advancing and retracting in the restricting portion, the rotation-preventing portion restricting an orientation around the axis of the operation wire.

9. The guide wire holder according to claim 8, wherein:
the restricting portion is provided at a distal end portion of the lumen, and
a proximal end of the restricted portion is disposed in the lumen.

10. A guide wire holder, comprising:
a sheath including a lumen and a central axis that extends longitudinally;

an operation wire that is inserted through the lumen, the operation wire configured to advance and retract along a longitudinal axis that is parallel to the central axis; and a hook that is continuous with a distal end of the operation wire and protrudes from a distal end of the sheath, wherein:

the sheath has an inner wall surface that includes a groove configured to extend from the distal end of the sheath to a proximal end side of the sheath and the groove having a concave shape that is recessed in a direction orthogonal to the central axis, the groove has an opening portion that opens to an outer peripheral surface of the sheath, the hook has a guide wire engagement surface configured to engage with a guide wire, the guide wire engagement surface and the inner wall surface are configured to hold the guide wire therebetween, a depth of the groove extends radially from the outer peripheral surface of the sheath towards the inner wall surface of the sheath, the groove includes a bottom portion that accommodates the guide wire along the central axis of the sheath, and the groove has an opening width that widens from the bottom portion of the groove toward the outer peripheral surface of the sheath.

11. The guide wire holder according to claim 10, wherein the depth of the groove that extends radially and is longer than a radius of the sheath.

12. A guide wire holder, comprising:

a sheath including a lumen and a central axis that extends longitudinally;

an operation wire that is inserted through the lumen, the operation wire configured to advance and retract along a longitudinal axis that is parallel to the central axis; and a hook that is continuous with a distal end of the operation wire and protrudes from a distal end of the sheath, wherein:

the sheath has an inner wall surface that includes a groove configured to extend from the distal end of the sheath to a proximal end side of the sheath and the groove having a concave shape that is recessed in a direction orthogonal to the central axis, the groove has an opening portion that opens to an outer peripheral surface of the sheath, the hook has a guide wire engagement surface configured to engage with a guide wire, the guide wire engagement surface and the inner wall surface are configured to hold the guide wire therebetween, the sheath has a restricting portion which is provided at a portion of the lumen along the longitudinal axis and in which an opening shape of the lumen in a cross section orthogonal to the longitudinal axis is an imperfect circle, the hook has a restricted portion formed by bending a rod-shaped member, and rotation of the operation wire around an axis thereof is restricted by locking the restricting portion and the restricted portion.

13. The guide wire holder according to claim 12, wherein:

a distal end portion of the sheath has a pre-curved portion in which the longitudinal axis is curved, a portion of the hook configured to be accommodated in the lumen has a first portion which extends more distally than the restricted portion and a second portion which extends more proximally than the restricted portion, the first portion is spaced from a curve of the pre-curved portion, and the second portion is located within the curve of the pre-curved portion.

* * * * *